United States Patent [19]
Fernholz et al.

[11] Patent Number: 6,060,455
[45] Date of Patent: May 9, 2000

[54] CATIONIC AND POLYCATIONIC AMPHIPHILES, REACTIVES CONTAINING THE SAME AND THEIR USE

[75] Inventors: Erhard Fernholz; Herbert Von Der Eltz, both of Weilheim; Matrhias Hinzpeter, München, all of Germany

[73] Assignee: Boehringer Mannheim GmbH, Mannheim, Germany

[21] Appl. No.: 08/952,970

[22] PCT Filed: Jun. 12, 1996

[86] PCT No.: PCT/EP96/02541

§ 371 Date: Dec. 5, 1997

§ 102(e) Date: Dec. 5, 1997

[87] PCT Pub. No.: WO97/00241

PCT Pub. Date: Jan. 3, 1997

[30] Foreign Application Priority Data

Jun. 14, 1995 [DE] Germany .......................... 195 21 412

[51] Int. Cl.⁷ ..................................... A61K 48/00

[52] U.S. Cl. ............................. 514/44; 435/455; 435/458; 536/23.1

[58] Field of Search ............................... 514/44; 536/23.1; 435/455, 458

[56] References Cited

U.S. PATENT DOCUMENTS

| 5,264,618 | 11/1993 | Felgner et al. | 560/224 |
| 5,747,471 | 5/1998 | Siegel et al. | 514/44 |
| 5,827,703 | 10/1998 | Debs et al. | 435/455 |

*Primary Examiner*—Bruce R. Campell
*Assistant Examiner*—Dave Trong Nguyen
*Attorney, Agent, or Firm*—Nikaido Marmelstein Murray & Oram, LLP.

[57] ABSTRACT

The invention concerns new cationic or polycationic amphiphiles which are capable of forming aggregates with macromolecules, in particular with DNA or RNA, and it concerns their delivery into prokaryotic or eukaryotic cells. Compounds with spermyl-dioleoyloxypropyl structure have proven to be particularly preferable.

16 Claims, 7 Drawing Sheets

Fig.3

1: $R_1$= $CH_3$; $R_2$= NHBoc
4: $R_1$= $(CH_2)_3$-NHBoc; $R_2$= NHBoc
10: $R_1$= $(CH_2)_3$- NBoc- $(CH_2)_3$- NHBoc; $R_2$= N(Boc)- $(CH_2)_3$- NHBoc

2: $R_1$= $CH_3$; $R_2$= NHBoc
5: $R_1$= $(CH_2)_3$-NHBoc; $R_2$= NHBoc
11: $R_1$= $(CH_2)_3$- NBoc- $(CH_2)_3$- NHBoc; $R_2$= N(Boc)- $(CH_2)_3$- NHBoc

CATIONIC AND POLYCATIONIC AMPHIPHILES, REACTIVES CONTAINING THE SAME AND THEIR USE

This application is the U.S. national phase of PCT application PCT/EP96/02541, filed Jun. 12, 1996, with a claim to the priority of German Application 19521412-9, filed Jun. 14, 1995.

BACKGROUND OF THE INVENTION

The invention concerns new cationic and polycationic amphiphiles which are capable of forming aggregates with macromolecules, in particular with DNA or RNA, and it concerns their delivery into prokaryotic or eukaryotic cells.

Amphiphiles (e.g. surfactants, detergents) have for some time played a general role in daily life. In contrast only recently has greater attention been paid to cationic amphiphiles through the pioneer work of Felgner since they can be used to deliver DNA and RNA into cells and transfect them in this manner (P. L. Felgner et al., *Proc. Natl. Acad. Sci., USA* 84, 7413–7417 (1987); P. Hawley-Nelson. WO 94/05624 et al., J. P. Behr, EP 0394111).

The individual reagents used for this are very varied. This is mostly due to the fact that they have been found empirically. Thus it has not been possible to specifically provide a compound for the application in question. Moreover the fact that compounds exist which only have an effect in a mixture with other reagents reveals the whole complexity of transfection. A review of most of the reagents that have been found up to now is given by Behr (*Bioconjugate Chem.*, 5, 382–389 (1994) and the references cited therein). However, in general the majority of the reagents can form liposomes.

The mechanism of transfection by cationic amphiphiles is still little understood. It appears plausible that the liposomes by means of their positive charge form a more positively charged complex with the DNA and this attaches itself to the negatively polarized cell membrane (P. L. Felgner, *Nature* 337, 387–388 (1989)). However, it is not certain how the penetration of the cell membrane and transport to the cell nucleus takes place.

Nevertheless, apart from the transfection efficiency it is possible to define a series of other requirements for new reagents:
- for efficiency it should not be necessary to pretreat the cells such as by permeabilizing the cell membrane with DMSO, a detergent such as digitonin or by scraping.
- the reagents should not be toxic if possible especially not at the most effective concentration and should be preferably biologically degradable
- it should be possible to use them equally for all cells that come into consideration
- they should not have a specificity for certain DNA molecules
- it should also be possible to use them in vivo. This means that in addition to toxicity, compatibility with serum is also of major significance. This has often been the reason for a drastic decrease in the transfection efficiency.

Hence the object of the invention was to provide appropriate reagents which equally fulfill these requirements.

SUMMARY OF THE INVENTION

This object is achieved by certain cationic, lipidic amphiphiles that can be used to deliver anionic compounds such as e.g. DNA into cells and in this process surprisingly exhibit improved properties with respect to the aforementioned requirements.

In particular compounds of the general formula I serve as amphiphiles in which
$R_1$ represents a saturated or unsaturated $C(O)$—$C_{1\text{-}23}$ or saturated or unsaturated $C_{1\text{-}24}$ group $A_1$ represents an O—$R_2$ group in which $R_2$ has the meaning stated for $R_1$ and can be the same as or different from $R_1$ $A_2$ represents an $NR_3X$ or an $N^+R_3R_4R_5Y^-$ residue in which
$R_3$, $R_4$ which are the same as one another or different, represent hydrogen, an alkyl group with 1 to 4 C atoms, a $(CH_2)_n$—OH or a $(CH_2)_n$—$NH_2$ group where n=2–6, $R_5$ which can be the same as or different from $R_3$ or $R_4$, denotes hydrogen, an alkyl group with 1 to 4 C atoms, a $(CH_2)_n$—OH, a $(CH_2)_n$-halogenide or a $((CH_2)_m NH)_o$—$(CH_2)_n$—$NH_2$ group in which m is an integer from 2 to 6 and can be equal to or different from n or o wherein n can be a number from 2 to 6 and o an integer from 0 to 4, X can, in addition to the meaning for $R_5$, have the following meaning: an amidically bound amino acid, an amidically bound peptide or polypeptide, a $C(O)$—$CHR_6N(R_7)_2$, a $C(O)CHR_6N^+(R_7)_3$, a $C(O)$—$CHR_6N^+(R_7)_2R_8$ or a $C(O)$—$CHR_6NR_7R_8$ group in which
$R_6$ can be a $(CH_2)_m$—$NR_7R_8$, a $(CH_2)_m$—$N^+(R_7)_2R_8$ or a $(CH_2)_m$—$N^+(R_7)_3$ residue
and m can be a number from 1 to 5,
$R_7$ represents hydrogen or an alkyl group with 1 to 4 C atoms,
$R_8$ represents a $(CH_2)_n$—$N(R_7)_2$ or $(CH_2)_n$—$N^+(R_7)_3$ group in which n is a number from 2 to 4 and $R_7$ can have the meaning stated above and Y is a pharmaceutically acceptable anion,
$B_1$ is an $NH[C(O)$—$(CH_2)_p$—$NH]_q$—Z residue in which p is a number from 1 to 6 and q is a number from 0 to 2,
Z represents an amidically bound amino acid, an amidically bound peptide or polypeptide, a $C(O)$—$CHR_6N(R_7)_2$, a $C(O)$—$CHR_6N^+(R_7)_3$, a $C(O)$—$CHR_6N^+(R_7)_2R_8$ or a $C(O)$—$CHR_6NR_7R_8$ group and $R_6$ to $R_8$ and m have the aforementioned meanings and $B_2$ can have the meaning stated for $A_1$ and the meaning for $A_1$ is only valid with $B_1$ and that of $A_2$ is only valid with $B_2$.

DESCRIPTION OF THE PREFERRED EMBODIMENTS

Those compounds are preferred in which the residues $R_1$ and $A_1$ have alkyl residues with 10 to 20 C atoms. In addition those compounds in which $A_2$ has the meaning $NR_3X$ are preferred and in particular those in which $R_3$ denotes hydrogen and X denotes an amidically bound amino acid, a suitable amino acid derivative, a peptide or polypeptide.

Suitable pharmaceutically acceptable anions Y are in particular halogenides, monomethylsulfate, acetate, trifluoroacetate and phosphate.

Figure 6:
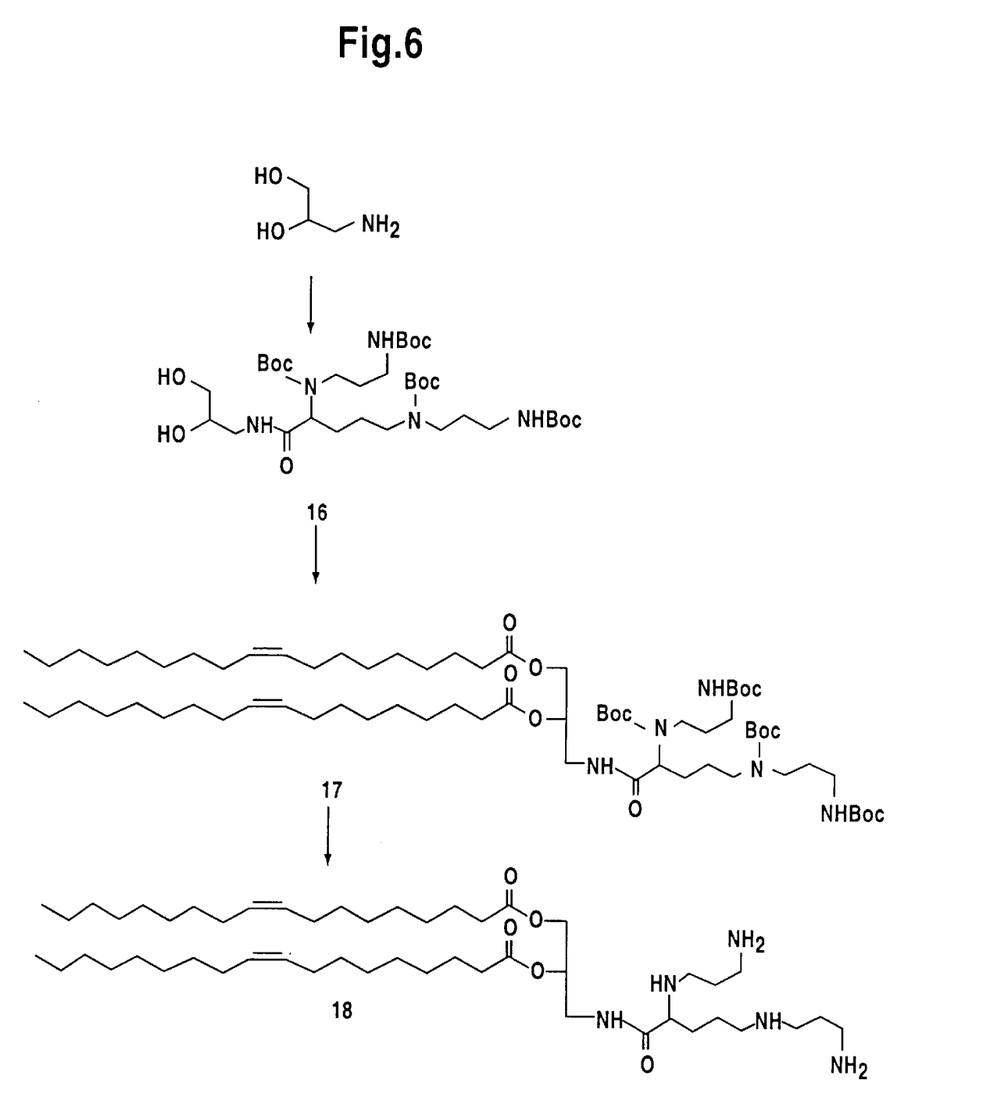
Figure 7:
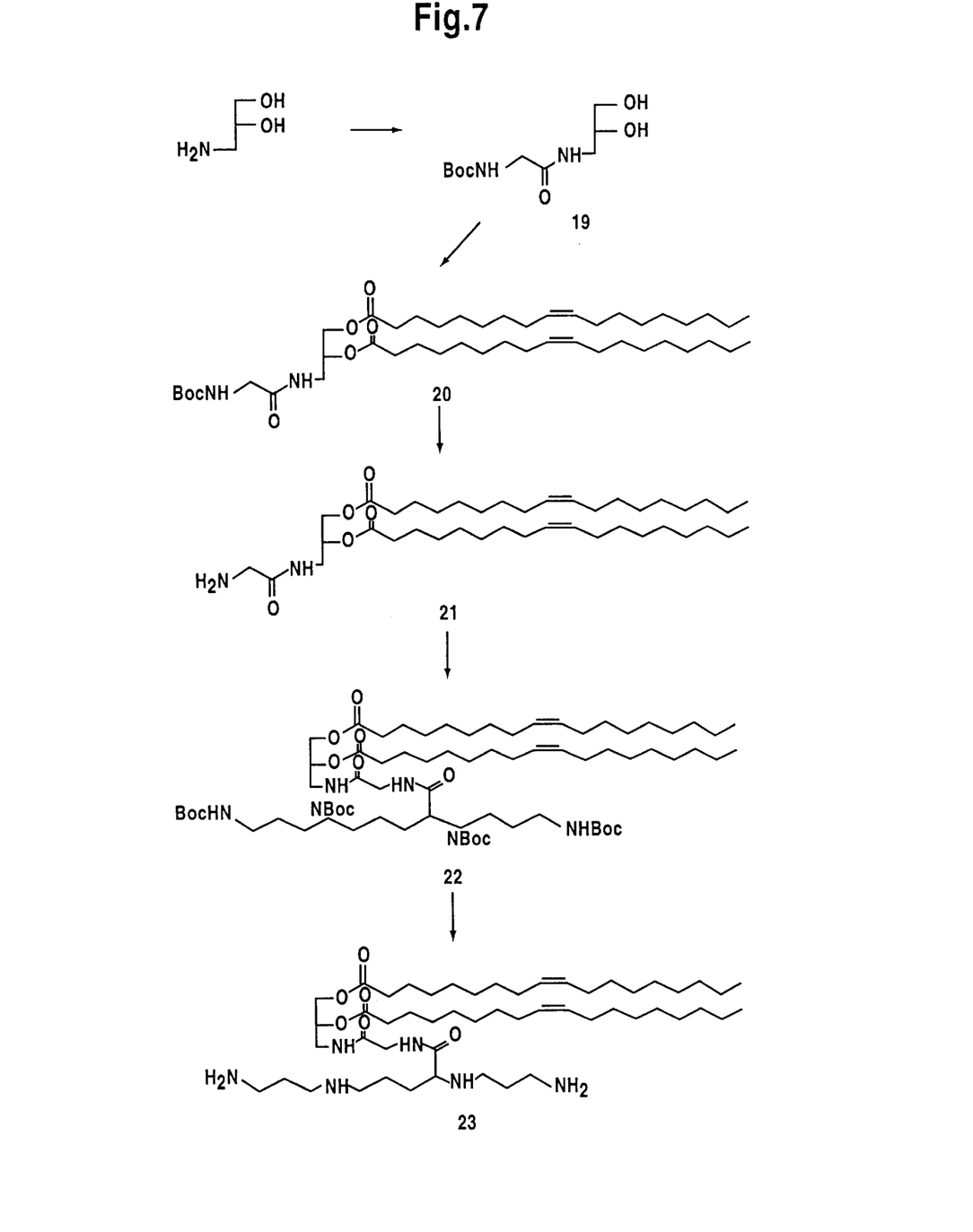

The following compounds according to the invention have proven to be particularly suitable: 2-(6-carboxyspermyl)-1,3-dioleoyloxy-propylamide, 2-(N,N,N,N',N',N'-hexamethylornithyl)-1,3-dioleoyloxy-propylamide, 1-(6-carboxyspermyl)-2,3-dioleoyloxy-propylamide and/or 2,3-dioleoyloxy-N-(N-(spermyl)-glycyl)-aminopropane as well as corresponding derivatives thereof. However, 2-(6-carboxyspermyl)-1,3-dimyristoyloxy-propylamide, 2-(1,1,1,5,5,10,10,14,14,14-decamethyl-6-carboxyspermyl)-1,3-dioleoyloxy-propylamide and/or 2-(N,N,N,N',N',N'-hexamethyllysyl)-1,3-dioleoyloxy-propylamide have also proven to be suitable Similar compounds such as for example amine and amidine derivatives of glycerol and propanediols such as e.g. 2-aminopropane compounds have already been described for other uses, a suitability for biological applications has however, not been suggested (DE-A-2835369; Woltrom et al., Journal of the Am.Soc. (1951) 73(8), p. 3553; Chem. Abs., 59(8), 1963, column 8586, FIG. 6).

Furthermore the present application also concerns the production of reagents with a transfection property. In this connection the new reagents can be used equally as a solution in a water-miscible solvent or as an aqueous liposomal formulation. When evaluating their transfection efficiency it was noted that:

in serum-free medium they already usually exhibit a better efficiency than other commercially available products, in serum-free medium they surprisingly allow a broader plateau of the DNA/reagent ratio with a similar transfection efficiency, they surprisingly had the same or a better efficiency in medium containing serum, the efficiency can be increased further by a liposomal formulation, surprisingly the compounds proved to be much less toxic than compounds with a similar transfection efficiency in a serum-free system.

Figure 1:
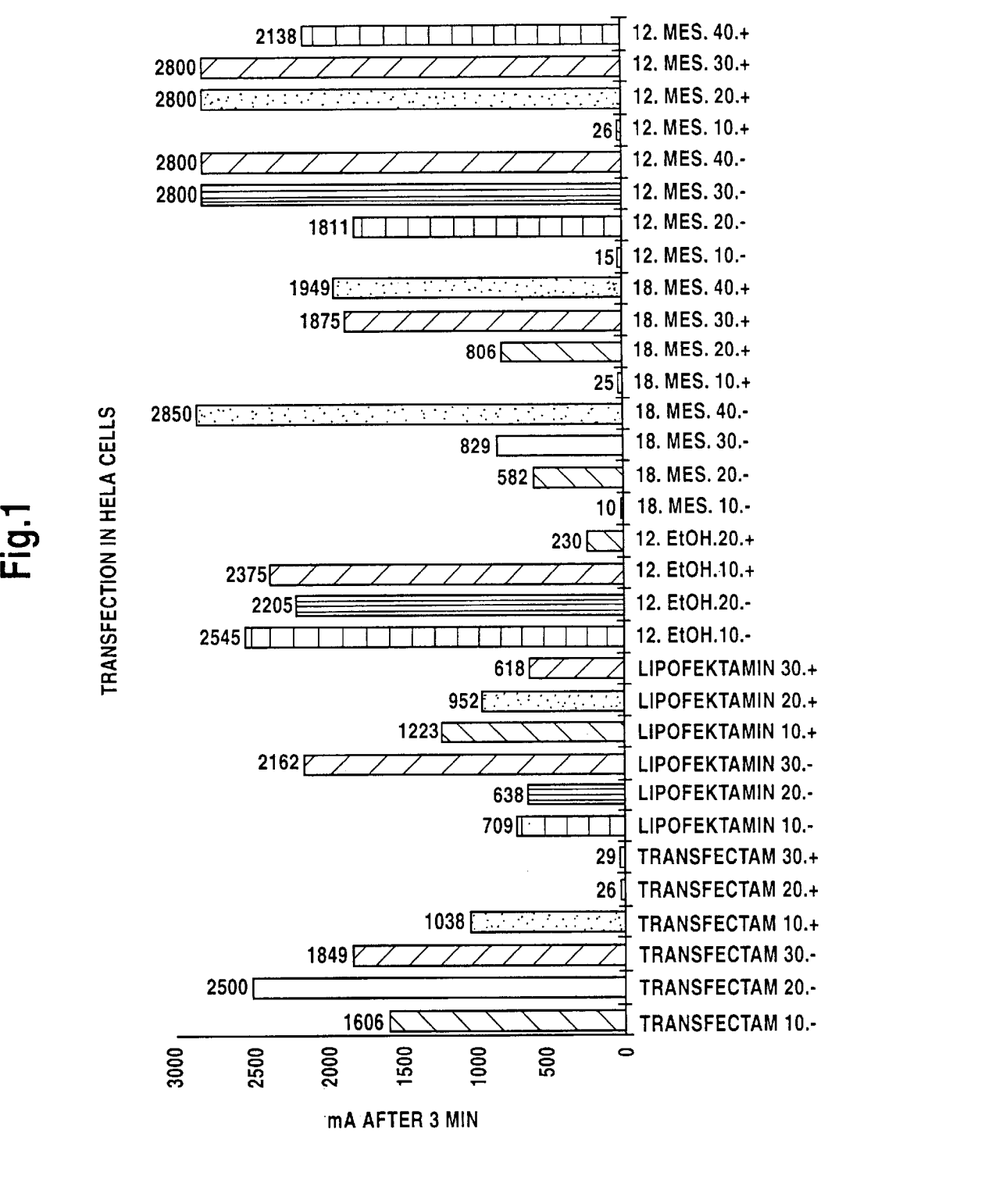
FIGS. 1 and 2 show the transfection efficiencies of selected compounds.
Figure 2:
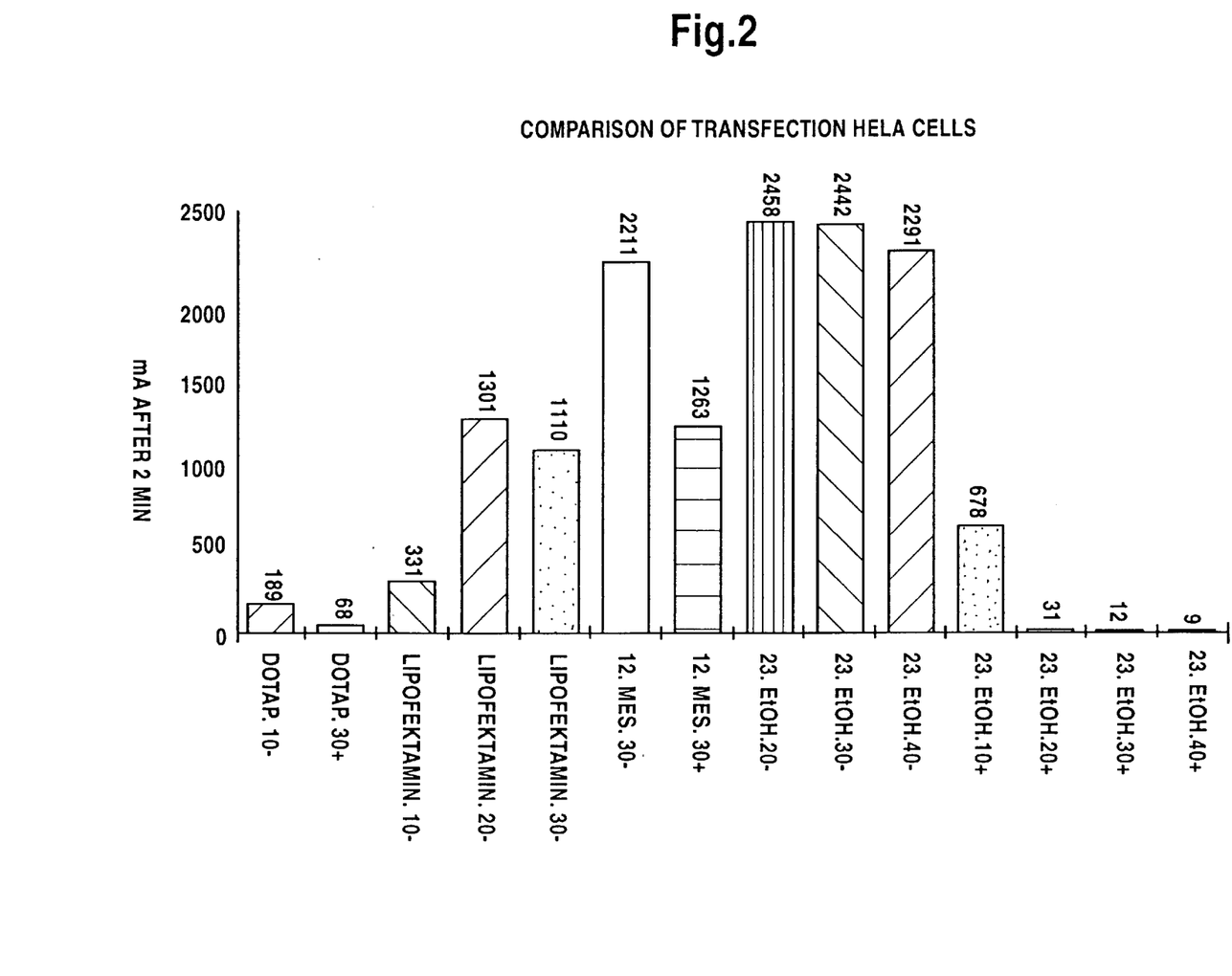
Figure 3:
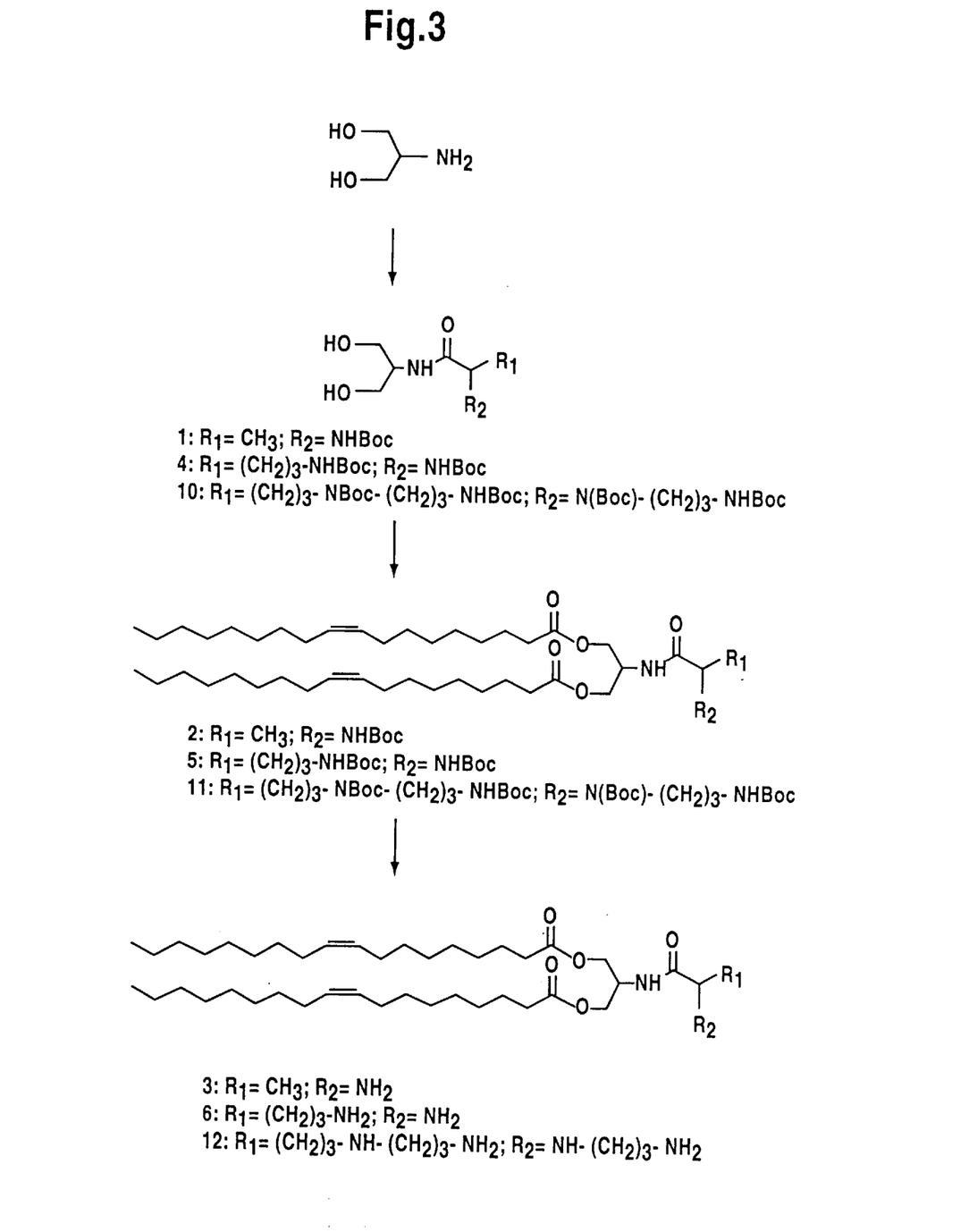
FIGS. 3 to 7 show appropriate reaction schemes for the synthesis of compounds according to the invention.
Figure 4:
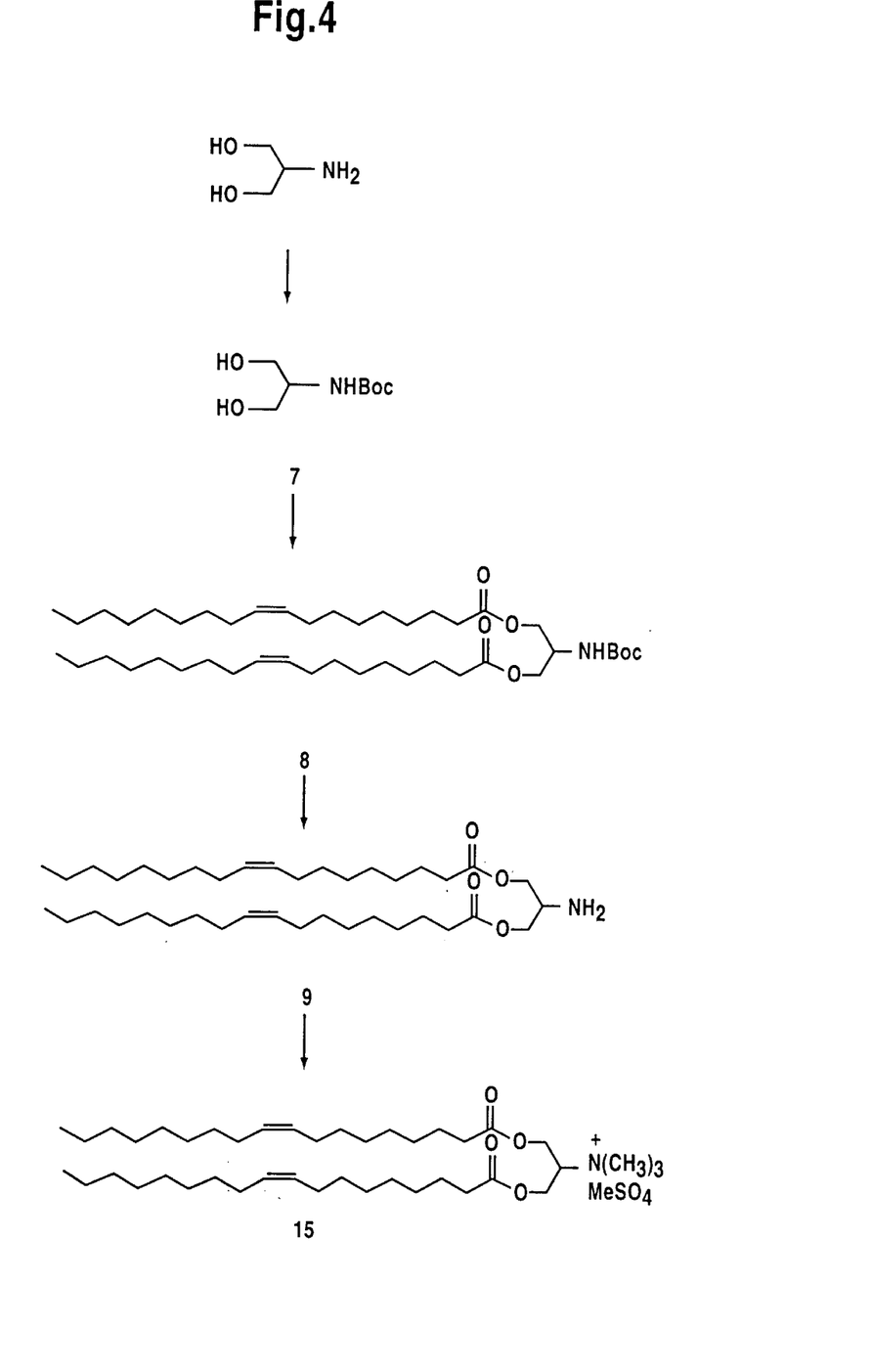
Figure 5:
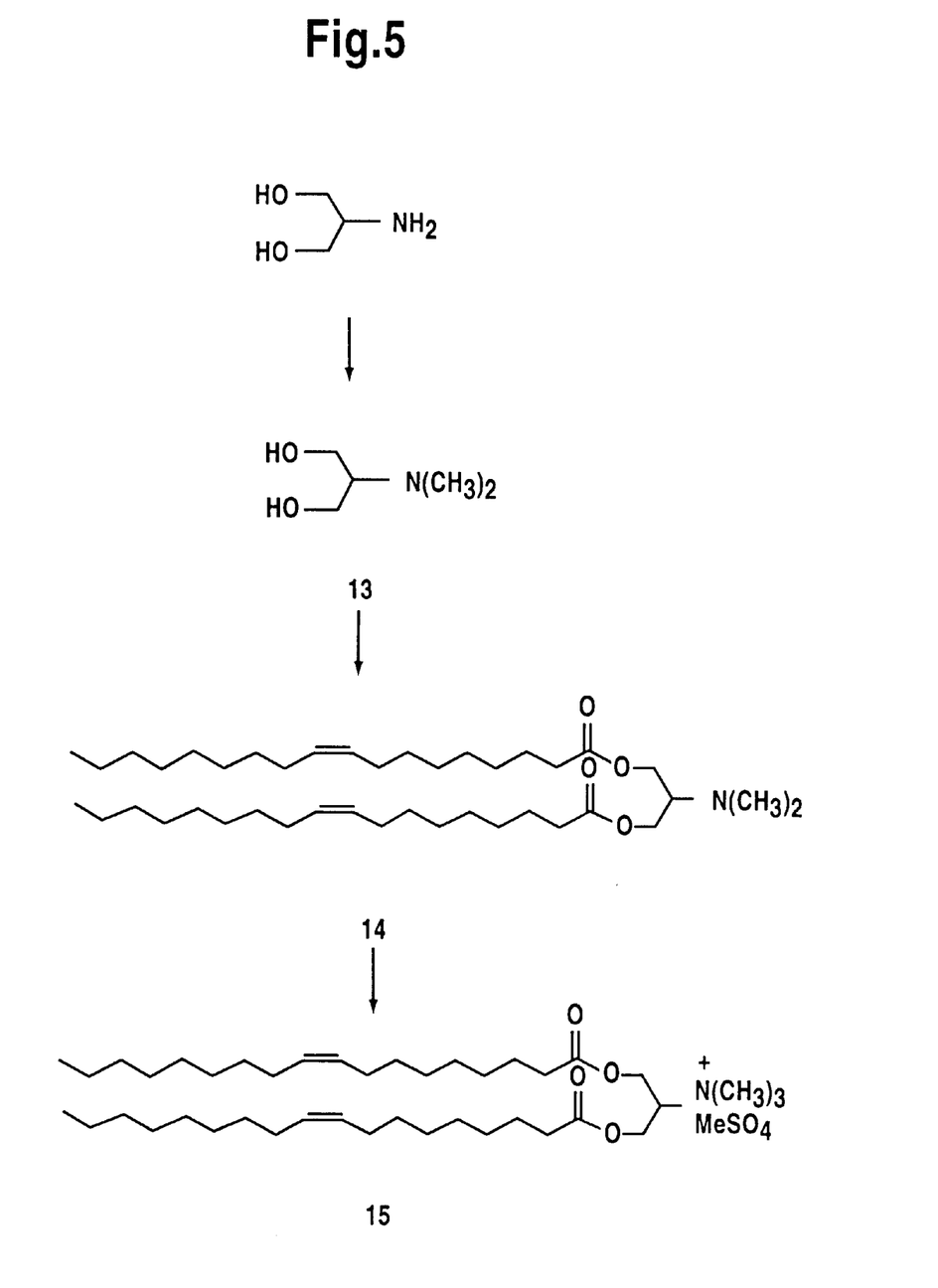

The transfection efficiencies of some selected compounds are shown in FIGS. 1 and 2 in comparison to known reagents.

The compounds according to the invention are synthesized by standard methods for a person skilled in the art (J. March: Advanced Organic Chemistry; John Wiley & Sons, 1985 and M. Bodanszky; Principles of Peptide Synthesis; Springer Verlag, 1984) and the end-products are optionally purified by chromatography in particular by ion exchanger chromatography. Appropriate reaction schemes are shown in FIGS. 3 to 7.

A prerequisite for the production of new transfection reagents was that the respective compounds are cationic and are suitable for aggregate formation since up to now it is above all such charged reagents that have resulted in a transfection (there are examples in which the DNA can be transported into the cell by means of uncharged reagents. However, for this they have to then be enclosed in liposomes during the preparation of which the molecule to be transported (e.g. DNA) may be damaged. In general the efficiency achieved by such complexes has not been very high (cf. e.g. A. Cudd, C. Nicolau in *Liposome Technology* (Gregoriadis Ed.), (1984) CRC Press Inc. Boca Raton, Fla.; S. F. Alino, M. Bobadilla, M. Garcia-Sanz, M. Lejarreta, F. Unda, E. Hilario in Biochem. Biophys. Res. Commun. 192, 174 (1993)).

A further starting point was that the compounds should be able to form liposomes. It is not clear why almost exclusively liposome-forming compounds are suitable for transfection. The latest findings (H. Gershon, R. Ghirlando, S. B. Guttman, A. Minsky in Biochemistry 32, 7143 (1993) and B. Sternberg, F. L. Sorgi, L. Huang in FEBS Letters 356, 361 (1994) show that they facilitate the formation of so-called meatball spaghetti structures which are required for transfection. It has still not been clarified whether the same applies to all reagents and in which form this contributes to passage through the cell membrane.

The following de novo syntheses resulted from these considerations which are shown in the diagrams of FIGS. 3 to 7.

In general several methods are available according to the state of the art for providing appropriate reagents such as for example pharmaceutical formulations. Liposomal and ethanolic formulations are used in particular whereby the efficiency of the various types of liposomes can already differ (for the preparation of liposomes see e.g. H. Schreier in "Pharmazie in unserer Zeit" 11, 97 (1982)).

However, the compounds according to the invention cannot only be used for transfection as liposomes but also in the form of other aggregates. In the case of liposome as well as in the case of aggregate formation other lipidic compounds can additionally be present apart from the compounds according to the invention. For example compounds from the phospholipid class are suitable for this; other compounds well-known to a person skilled in the art could also be used.

It must also be regarded as surprising that liposomes can be formed from the compounds according to the invention of type 3, 6, 12 or 15 (see examples 3, 6, 12 and 15) which are described here for the first time.

The transfection was carried out on HeLa cells with the pSV2-CAT plasmid as an example (Gorman, C. M. et al., Mol. Cell. Biol. 2, 1044–1051 (1982)). The transfection efficiency is determined by the CAT-ELISA kit (Boehringer Mannheim GmbH) and is shown in FIGS. 1 and 2 in comparison to known reagents.

Due to their low toxicity these compounds (alone or in combination with other lipidic compounds) can also be used in vivo.

The invention is elucidated further by the following examples.

EXAMPLE 1

Synthesis of 2-(N-tert.-butyloxycarbonyl-L-alanyl)-1,3-dihydroxy propylamide 1

756 mg (4 mmol) Boc-L-alanine and 600 µl (4.3 mmol) triethylamine dissolved in 10 ml absolute THF were placed in a round-bottom flask with a bubble counter and cooled to −10° C. Then 320 µl (4 mmol) methyl chloroformate was added and it was stirred for 30 minutes at 0° C. After addition of 456 mg (5 mmol) 2-amino-1,3-propanediol sufficient water was added to form a homogeneous solution and it was stirred for a further 1 h at room temperature. After removing the THF 50 ml ethyl acetate was added. The organic phase was washed with saturated $NaHCO_3$ solution and saturated NaCl solution and dried over $Na_2SO_4$. After removing the solvent 332 mg (32%) of a colourless oil was obtained.

$^1$H-NMR (CDCl$_3$): δ=1.32 (d; 3 H; J=7.1 Hz; CH—CH$_3$); 1.40 (s; 9 H; C(CH$_3$)$_3$); 3.55–3.85 (m; 4 H; CH(CH$_2$OH)$_2$); 3.85–4.0 m; 1 H; NH—CH); 4.0–4.5 (m; 3 H; NH—CH, 2×OH); 5.6–5.8 (m; 1 H; NH—CH(CH$_2$OH)$_2$); 7.0–7.35 (m; 1 H; OOC—NH—CH).

$^{13}$C-NMR (CDCl$_3$): δ=18.4 (CH—CH$_3$); 28.2 (C(CH$_3$)$_3$), 52.2 (NH—CH—CO); 52.4 (CH(CH$_2$OH)$_2$); 61.8 (CH(CH$_2$OH)$_2$); 80.2 (C(CH$_3$); 155.7 (NH—COO); 173.8 (CH—CO—NH).

EXAMPLE 2

Synthesis of 2-(N-tert.-butyloxycarbonyl-L-alanyl)-1,3-dioleoyloxy propylamide 2

A solution of 598 mg (2.28 mmol) 1, 1.610 g (5.70 mmol) oleic acid, 1.176 g (5.70 mmol) DCC and 28 mg (0.23 mmol) dimethylaminopyridine in 40 ml abs. CH$_2$Cl$_2$ was stirred overnight at room temperature in a round-bottom flask. Subsequently it was filtered and the filtrate was rotary evaporated. The crude product was purified by column chromatography (silica gel, CH$_2$Cl$_2$:MeOH=30:1). 1.450 g (80%) of a colourless oil was obtained.

$^1$H-NMR (CDCl$_3$): δ=0.87 (t; 6 H; J=6.6 Hz; 2×CH$_2$—CH$_3$); 1.15–1.5 (m; 43 H; CH—CH$_3$, 2×CO—(CH$_2$)$_2$—(CH$_2$)$_4$, 2×(CH$_2$)$_6$—CH$_3$); 1.43 (s; 9 H; C(CH$_3$)$_3$); 1.5–1.7 (m; 4 H; 2×CO—CH$_2$—CH$_2$); 1.9–2.1 (m; 8 H; 2×CH$_2$—CH=CH—CH$_2$); 2.30 (t, 4 H; J=7.6 Hz; 2×CO—CH$_2$); 4.0–4.25 (m; 5 H; NH—CH; 2×CH$_2$OOC); 4.35–4.5 (m; 1 H; NH—CH); 4.9–5.0 (m; 1 H; NH—CH—CH$_2$); 5.25–5.45 (m; 4 H; 2×CH=CH); 6.5–6.65 (m; 1 H; OOC—NH—CH).

$^{13}$C-NMR (CDCl$_3$): δ=14.0 (2×C(18)H$_3$); 22.5 (2×C(17)H$_2$); 24.7 (2×C(3)H$_2$); 27.0, 27.1, 28.98, 29.04, 29.2, 29.4, 29.56, 29.62 {2×[C(4)H$_2$—C(7)H$_2$, C(12)H$_2$—C(16)H$_2$]}; 28.1 (C(CH$_3$)$_3$); 31.8 (2×C(2)H$_2$); 33.87, 33.88 {2×[C(8)H$_2$, C(11)H$_2$]}; 47.2 (CH(CH$_2$O$_2$C—R)$_2$); 62.4 (CH(CH$_2$O$_2$C—R)$_2$); 129.6, 129.9 (2×CH=CH); 172.4 (CH—CO—NH); 173.4 (CH$_2$—COO).

EXAMPLE 3

Synthesis of 2-L-alanyl-1,3-dioleoyloxy-propylamide 3

702 mg (0.89 mmol) 2 dissolved in 6 ml abs. CH$_2$Cl$_2$ was placed in a round-bottom flask with a bubble counter and 2 ml (26.12 mmol) TFA was added. After 30 min stirring at room temperature the reaction mixture was transferred to a separating funnel and 50 ml CH$_2$Cl$_2$ as well as 28 ml 1 N NaOH was added. The organic phase was washed with 10 ml saturated NaHCO$_3$ solution and dried over Na$_2$SO$_4$. After removing the solvent 599 mg (97%) of a nearly colourless oil was obtained.

$^1$H-NMR (CDCl$_3$): δ=0.75–0.9 (m; 6 H; 2×CH$_2$—CH$_3$); 1.1–1.4 (m; 43 H; CH—CH$_3$, 2×CO—(CH$_2$)$_2$—(CH$_2$)$_4$, 2×(CH$_2$)$_6$—CH$_3$); 1.4–1.7 (m; 6 H; NH$_2$, 2×CO—CH$_2$—CH$_2$); 1.85–2.1 (m; 8 H; 2×CH$_2$—CH=CH—CH$_2$); 2.30 (t, 4 H; J=7.5 Hz; 2×CO—CH$_2$); 3.35–3.55 (m; 1 H; NH—CH); 4.0–4.25 (m; 4 H; 2×CH$_2$OOC); 4.3–4.5 (m; 1 H; NH—CH); 5.2–5.4 (m; 4 H; 2×CHH=CH); 7.5–7.65 (m; 1 H; CO—NH—CH).

$^{13}$C-NMR (CDCl$_3$): δ=14.0 (2×C(18)H$_3$); 22.5 (2×C(17)H$_2$); 24.7 (2×C(3)H$_2$); 27.0, 27.1, 28.9, 29.0, 29.2, 29.4, 29.5, 29.6 {2×[C(4)H$_2$—C(7)H$_2$, C(12)H$_2$—C(16)H$_2$]}; 31.7 (2×C(2)H$_2$); 33.9 {2×[C(8)H$_2$, C(11)H$_2$]}; 46.7 (CH(CH$_2$O$_2$C—R)$_2$); 62.5 (CH(CH$_2$O$_2$C—R)$_2$); 129.5, 129.8 (2×CH=CH); 173.3 (CH—CO—NH); 173.4 (CH$_2$—COO).

EXAMPLE 4

Synthesis of 2-(N,N'-di-tert.-butyloxycarbonyl-L-ornithyl)-1,3-dihydroxypropylamide 4

2.000 g (6 mmol) Boc-L-ornithine and 900 μl (6.45 mmol) triethylamine dissolved in 25 ml absolute THF were placed in a round-bottom flask with a bubble counter and cooled to −10° C. Then 480 μl (6 mmol) methyl chloroformate was added and it was stirred for 30 minutes at 0° C. After addition of 684 mg (7.5 mmol) 2-amino-1,3-propanediol sufficient water was added to form a homogeneous solution and it was stirred for a further 1 h at room temperature. After removing the solvent it was taken up in ethyl acetate, washed with saturated NaHCO$_3$ solution and saturated NaCl solution and dried over Na$_2$SO$_4$. After removing the solvent 1.987 g (82%) 4 was obtained as colourless crystals.

$^1$H-NMR (CDCl$_3$): δ=1.42 (s; 9 H; C(CH$_3$)$_3$); 1.4–1.95 (m; 4 H; CH$_2$—CH$_2$—CH$_2$—NH); 3.0–3.2 (m; 2 H; CH$_2$NH); 3.6–3.8 (m; 4 H; CH(CH$_2$OH)$_2$); 3.9–4.05 (m; 1 H; NH—CH); 4.05–4.6 (m; 3 H; NH—CH, 2×OH); 5.2–5.4 (m; 1 H; NH—CH); 5.8–6.05 (m; 1 H; NH—CH); 7.35–7.5 (m; 1 H; NH—CH).

$^{13}$C-NMR (CDCl$_3$): δ=26.1 (CH$_2$—CH$_2$—CH$_2$—NH); 28.4 (C(CH$_3$)$_3$, 28.5 (C(CH$_3$)$_3$); 30.1 (CH$_2$—CH$_2$—NH); 40.0 (CH$_2$—NH); 52.9 (CH(CH$_2$OH)$_2$); 54.4 (NH—CH—CO); 61.8 (CH(CH$_2$OH)$_2$); 79.3 (C(CH$_3$)$_3$); 80.1 (C(CH$_3$)$_3$); 156.1 (NH—COO); 156.5 (NH-COO); 173.3 (CH—CO—NH).

EXAMPLE 5

Synthesis of 2-(N,N'-di-tert.-butyloxycarbonyl-L-ornithyl)-1,3-dioleoxy-propylamide 5

A solution of 1.898 g (4.68 mmol) 4, 3.305 g (11.7 mmol) oleic acid, 2.414 g (11.7 mmol) DCC and 57 mg (0.47 mmol) dimethylaminopyridine in 50 ml abs. CH$_2$Cl$_2$ was stirred overnight at room temperature in a round-bottom flask. Subsequently it was filtered and the filtrate was rotary evaporated. The crude product was purified by column chromatography on silica gel (CH$_2$Cl$_2$:MeOH=30:1). 1.678 g (38%) of the product was obtained as a colourless wax-like solid of melting point 52–54° C.

$^1$H-NMR (CDCl$_3$): δ=0.75–0.9 (m; 6 H; 2×CH$_2$—CH$_3$); 1.05–1.5 (m; 40 H; 2×CO—(CH$_2$)$_2$—(CH$_2$)$_4$, 2×(CH$_2$)$_6$—CH$_3$); 1.42 (s; 18 H; 2×C(CH$_3$)$_3$; 1.45–1.85 (m; 8 H; 2×CH$_2$—CH$_2$—CH$_2$—NH, 2×CO—CH$_2$—CH$_2$); 1.85–2.1 (m, 8 H; 2×CH$_2$—CH=CH—CH$_2$); 2.2–2.35 (m; 4 H; 2×CO—CH$_2$); 3.0–3.35 (2 m; 2 H; CH$_2$—NH); 4.0–4.25 (m; 5 H; NH—CH; 2×CH$_2$OOC); 4.35–4.5 (m; 1 H; NH—CH); 4.7–4.8 (m; 1H; NH—CH); 5.1–5.2 (m; 1 H; NH—CH); 5.2–5.4 (m; 4 H; 2×CH=CH); 6.65–6.8 (m; 1 H; OOC—NH—CH).

$^{13}$C-NMR (CDCl$_3$): δ=14.0 (2×C(18)H$_3$); 22.5 (2×C(17)H$_2$); 24.6 (2×C(3)H$_2$); 26.2 (CH$_2$—CH$_2$—CH$_2$—NH); 27.0, 27.1, 28.97, 29.04, 29.2, 29.4, 29.56, 29.61 {2×[C(4)H$_2$—C(7)H$_2$, C(12)H$_2$—C(16)H$_2$] and CH$_2$—CH$_2$—NH}; 28.1, 28.3 (2×C(CH$_3$)$_3$); 31.7 (2×C(2)H$_2$); 33.85, 33.86 {2×[C(8)H$_2$, C(11)H$_2$]}; 47.2 (CH(CH$_2$O$_2$C—R)$_2$); 62.3 (CH(CH$_2$O$_2$C—R)$_2$); 129.6, 129.8 (2×CH=CH); 156.3 (NH—COO); 173.30, 173.33 (CH—CO—NH, 2×CH$_2$—COO).

EXAMPLE 6

Synthesis of 2-L-ornithyl-1,3-dioleoyloxy-propylamide 6

421 mg (0.451 mmol) 5 dissolved in 3 ml abs. CH$_2$Cl$_2$ was placed in a round-bottom flask and 1 ml (13.06 mmol)

TFA was added. After stirring for 30 min. at room temperature the reaction mixture was diluted with 200 ml $CH_2Cl_2$, washed twice with saturated $NaHCO_3$ solution and dried over $Na_2SO_4$. After removing the solvent, 296 mg (89%) of an almost colourless oil was obtained.

$^1$H-NMR ($CDCl_3$): δ=0.86 (t; 6 H; J=6.7 Hz; 2×$CH_2$—C$\underline{H}_3$); 1.1–1.45 (m; 40 H; 2×CO—($CH_2$)$_2$—($C\underline{H}_2$)$_4$, 2×(C$\underline{H}_2$)$_6$—$CH_3$); 1.45–1.7 (m; 8 H; C$\underline{H}_2$—C$\underline{H}_2$—$CH_2$—$NH_2$, 2×CO—($CH_2$—C$\underline{H}_2$); 1.9–2.1 (m; 8 H; 2×C$\underline{H}_2$—CH=CH—C$\underline{H}_2$); 2.30 (t; 4 H; J=7.5 Hz; 2×CO—C$\underline{H}_2$); 2.6–3.1 (m; 4 H; 2×$NH_2$); 3.15–3.55 (m; 2 H; C$\underline{H}_2$—$NH_2$); 3.55–3.75 (m; 1 H; NH—C$\underline{H}$); 4.0–4.25 (m; 4 H; 2×C$\underline{H}_2$—OOC); 4.3–4.5 (m; 1 H; NH—C$\underline{H}$); 5.2–5.4 (m; 4 H; 2×C$\underline{H}$=CH); 7.65–7.75 (m; 1 H; CO—N$\underline{H}$—CH).

$^{13}$C-NNR ($CDCl_3$): δ=14.0 (2×C(18)$H_3$); 22.5 (2×C(17)$H_2$); 24.7 (2×C(3)$H_2$); 26.99, 27.04, 29.1, 29.3, 29.5, 29.6, {2×[C(4)$H_2$—C(7)$H_2$, C(12)$H_2$—C(16)$H_2$], $\underline{C}H_2$—$CH_2$—$\underline{C}H_2NH$}; 31.7, (2×C(2)$H_2$); 33.9 (2×[C(8)$H_2$, C(11)$H_2$]); 46.7 ($\underline{C}H(CH_2O_2C$—R)$_2$); 54.6 ($NH_2$—$\underline{C}H$—CO); 62.5 (CH($\underline{C}H_2O_2C$—R)$_2$); 129.5, 129.8 (2×CH=CH); 173.31, 173.6 (CH—$\underline{C}O$—NH, 2×$CH_2$—$\underline{C}OO$); 174.7 (CH—$\underline{C}O$—NH).

EXAMPLE 7

Synthesis of N-tert.-butyloxycarbonyl-1,3-dihydroxy-propylamine 7

A solution of 1.07 (5 mmol) $Boc_2O$, 697 μl (5 mmol) triethylamine and 456 mg (5 mmol) 2-amino-1,3-propanediol in 10 ml THF/water (1:1) was stirred overnight at room temperature in a round-bottom flask. After removing the THF on a rotary evaporator, 50 ml ethyl aceatate and 10 ml saturated NaCl solution was added. The organic phase was washed with 10 ml saturated NaCl solution and dried over $Na_2SO_4$. After removing the solvent 589 mg (62%) 7 was obtained as colourless crystals. Melting point 83–85° C.

$^1$H-NMR ($CDCl_3$): δ=1.44 (s; 9 H; C(C$\underline{H}_3$)$_3$); 3.4–3.85 (m; 7 H; CH($CH_2OH$)$_2$); 5.3–5.45 (m; 1 H; N$\underline{C}$—CH).

$^{13}$C-NMR ($CDCl_3$): δ=28.4 (C(C$\underline{H}_3$)$_3$); 53.3 ($\underline{C}H(CH_2OH)_2$); 62.6 (CH($\underline{C}H_2OH$)$_2$); 79.9 ($\underline{C}(CH_3)_3$); 156.5 (NH—$\underline{C}OO$).

EXAMPLE 8

Synthesis of N-tert.-butyloxycarbonyl-1,3-dioleoyloxy-propylamine 8

A solution of 478 mg (2.5 mmol) 7, 1.695 g (6 mmol) oleic acid, 1.28 g (6 mmol) DCC and 12 mg (0.1 mmol) dimethylaminopyridine in 25 ml abs. $CH_2Cl_2$ was stirred overnight at room temperature in a round-bottom flask. Subsequently it was filtered and the filtrate was rotary evaporated. The crude product was purified by column chromatography on silica gel (hexane:ethyl acetate=5:1). 1.482 g (82%) of the product was obtained as a colourless oil.

$^1$H-NMR ($CDCl_3$): δ=0.86 (t; 6 H; J=6.6 Hz; 2×$CH_2$—C$\underline{H}_3$); 1.1–1.5 (m; 40 H; 2×CO—($CH_2$)$_2$—($C\underline{H}_2$)$_4$, 2×(C$\underline{H}_2$)$_6$—$CH_3$);.1.43 (s; 9 H; C(C$\underline{H}_3$); 1.5–1.7 (m; 4 H; 2×CO—$CH_2$—C$\underline{H}_2$); 1.9–2.1 (m, 8 H; 2×C$\underline{H}_2$—CH=CH—C$\underline{H}_2$); 2.30 (t; 4 H; J=7.5 Hz; 2×CO—C$\underline{H}_2$); 3.95–4.25 (m; 5 H; NH—C$\underline{H}$; 2×C$\underline{H}_2$OOC); 4.7–4.85 (m; 1 H; OOC—N$\underline{H}$—CH); 5.25–5.45 (m; 4 H; 2×C$\underline{H}$=C$\underline{H}$).

$^{13}$C-NMR ($CDCl_3$): δ=14.0 (2×C(18)$H_3$); 22.5 (2×C(17)$H_2$); 24.7 (2×C(3)$H_2$); 27.0, 27.1, 28.96, 29.02, 29.2, 29.4, 29.55, 29.62 {2×[C(4)$H_2$—C(7)$H_2$, C(12)$H_2$—C(16)$H_2$]}; 28.2 (C(C$\underline{H}_3$)$_3$); 31.8 (2×C(2)$H_2$); 33.9 {2×[C(8)$H_2$, C(11)$H_2$]}; 48.4 ($\underline{C}H(CH_2O_2C$—R)$_2$); 62.8 (CH($\underline{C}H_2O_2\underline{C}$—R)$_2$); 79.8 ($\underline{C}(CH_3)_3$); 129.6, 129.8 (2×CH=CH); 154.9 (NH—$\underline{C}$OO); 173.3 ($CH_2$—$\underline{C}$OO).

EXAMPLE 9

Synthesis of 1,3-dioleoyloxy-propylamine 9

720 mg (1 mmol) 8, dissolved in 3 ml abs. $CH_2Cl_2$ was placed in a round-bottom flask and 1 ml (13.06 mmol) TFA was added. After stirring for 30 min. at room temperature the reaction mixture was diluted with 50 ml $CH_2Cl_2$, washed with saturated $NaHCO_3$ solution and dried over $Na_2SO_4$. After removing the solvent 589 mg (95%) of a colourless oil was obtained.

$^1$H-NMR ($CDCl_3$): δ=0.87 (t; 6 H; J=6.6 Hz; 2×$CH_2$—C$\underline{H}_3$); 1.1–1.5 (m; 40 H; 2×CO—($CH_2$)$_2$—($C\underline{H}_2$)$_4$, 2×(C$\underline{H}_2$)$_6$—$CH_3$); 1.35–1.5 (m; 2 H; CH—N$\underline{H}_2$); 1.5–1.7 (m; 4 H; 2×CO—($CH_2$—C$\underline{H}_2$); 1.85–2.1 (m; 8 H; 2×C$\underline{H}_2$—CH=CH—C$\underline{H}_2$); 2.32 (t; 4 H; J=7.5 Hz; 2×CO—C$\underline{H}_2$); 3.2–3.35 (m; 1 H; C$\underline{H}$—$NH_2$); 3.95–4.15 (m; 4 H; 2×C$\underline{H}_2$—OOC); 5.25–5.45 (m; 4 H; 2×C$\underline{H}$=CH).

$^{13}$C-NMR ($CDCl_3$): δ=14.0 (2×C(18)$H_3$); 22.5 (2×C(17)$H_2$); 24.8 (2×C(3)$H_2$); 27.0, 27.1, 28.96, 28.99, 29.03, 29.2, 29.4, 29.55, 29.63 {2×[C(4)$H_2$—C(7)$H_2$, C(12)$H_2$—C(16)$H_2$]}; 31.8, (2×C(2)$H_2$); 34.0 (2×[C(8)$H_2$, C(11)$H_2$]); 49 {$\underline{C}H(CH_2O_2C$—R)$_2$}; 65.7 {CH($\underline{C}H_2O_2C$—R)$_2$}; 129.6, 129.9 (2×CH=CH); 173.4 ($CH_2$—$\underline{C}$OO).

EXAMPLE 10

Synthesis of 2-(N,N',N'',N'''-tetra-tert.-butyloxycarbonyl-6-carboxy-spermyl)-1,3-dihydroxy-propylamide 10

25 μl (312 μmol) methyl chloroformate was added at –10° C. to a solution of 202 mg (312 μmol) tetra-Boc-spermine and 47 μl (335 μmol) triethylamine in 2 ml abs. THF and stirred for 30 min at 0° C.

After subsequent addition of 36 mg (390 μmol) 2-amino-1,3-propanediol sufficient water was added to form a homogeneous emulsion and afterwards it was stirred for a further 1 h at room temperature. After removing the sovent on a rotary evaporator ca. 30 ml ethyl acetate was added. The organic phase was washed with saturated $NaHCO_3$ solution and saturated NaCl solution and dried over $Na_2SO_4$. After removing the solvent 208 mg (93%) of a colourless, foamy solid was obtained.

$^1$H-NMR ($CDCl_3$): δ=1.3–1.47 (m; 36 H; 4×C($CH_3$)$_3$); 1.5–2.05 (m; 8 H; 2×N—$CH_2$—C$\underline{H}_2$—$CH_2$—N, N—CH—C$\underline{H}_2$—C$\underline{H}_2$—$CH_2$—N); 2.85–3.4 (m; 10 H; 5×N—C$\underline{H}_2$); 3.65–3.8 (m; 4 H; 2×C$\underline{H}_2$—OH); 3.8–4.5 (m; 4 H; 2×—CH—, 2×$CH_2$—O$\underline{H}$); 4.8–5.1 (s(broad); 1 H; $CH_2$—N$\underline{H}$); 5.25–5.4 (s(broad); 1 H; $CH_2$—NH); 7.05–7.15 (s(broad); 1 H; N$\underline{H}$—CO).

$^{13}$C-NMR ($CDCl_3$): δ=25.0, 29.5 (N—CH—$\underline{C}H_2$—$\underline{C}H_2$—$CH_2$—N); 28.0, 28.2, 28.3 (4×C($\underline{C}H_3$)$_3$); 38.0, 38.1 (2×N—$\underline{C}H_2$—$\underline{C}H_2$—$CH_2$—N); 42.9, 45.0, 47.0 (other spermyl-$CH_2$ carbons); 52.4 ($\underline{C}H(CH_2$—OH)$_2$); 59.8 ($\underline{C}H$—CO); 63.1 (CH($\underline{C}H_2$—OH)$_2$); 79.3, 79.5, 81.1 (4×CO—O—$\underline{C}$)$CH_3$)$_3$); 156.0, 156.1 (4×CO—O—$\underline{C}$)$CH_3$)$_3$); 171.1 ($\underline{C}O$—NH).

EXAMPLE 11

Synthesis of 2-(N,N',N'',N'''-tetra-tert.-butyloxycarbonyl-6-carboxy-spermyl)-1,3-dioleoyloxy-propylamide 11

A solution of 208 mg (72 μmol) 10, 204 mg (289 μmol) oleic acid, 149 mg (723 μmol) DCC and 4 mg (29 μmol)

dimethylamino-pyridine in 6 ml abs. $CH_2Cl_2$ was stirred overnight at room temperature in a closed round-bottom flask.

Subsequently it was filtered, rewashed with hexane/ether (3:1) and the filtrate was rotary evaporated. After column chromatography on silica gel ($CH_2Cl_2$/MeOH=20:1). 160 mg (44%) of a colourless oil was obtained.

$^1$H-NMR (CDCl$_3$): δ=0.8–0.95 (m; 6 H; 2×CH$_2$—C$\underline{H}_3$); 1.2–1.4 (m; 40 H; 2×CO—(CH$_2$)$_2$—(C$\underline{H}_2$)$_4$, 2×(CH$_2$)$_6$—CH$_3$); 1.4–1.55 (m; 36 H; 4×C(C$\underline{H}_3$)$_3$); 1.55–1.75 (m; 10 H; 3×(—CH$_2$—C$\underline{H}_2$—CH$_2$—)$_{sperm}$, 2×CO—CH$_2$—C$\underline{H}_2$—); 1.85–2.05 (m, 10 H; (—CH—C$\underline{H}_2$—CH$_2$—)$_{sperm}$, 2×C$\underline{H}_2$—CH=CH—CH$_2$); 2.25–2.35 (m; 4 H; 2×CO—C$\underline{H}_2$); 3.0–3.35 (m, 10 H; 5×N—C$\underline{H}_2$); 4.0–4.4 (m; 6 H; 2×C$\underline{H}$—N, (CH(C$\underline{H}_2$O$_2$C—R)$_2$); 4.5–5.1 (s(very broad); 1 H; N$\underline{H}$—CH$_2$); 5.25–5.35 (m; 4 H; 2×C$\underline{H}$=C$\underline{H}$); 6.8–7.0 (s(broad); 1 H; N$\underline{H}$—CO).

$^{13}$C-NMR (CDCl$_3$): δ=14.4 (2×C(18)H$_3$); 23.0 (2×C(17)H$_2$); 25.2 (2×C(3)H$_2$); 27.6 (C(8)H$_2$,C(11)H$_2$); 29.5, 29.6, 29.7, 29.9, 30.1, 32.3 ((CH—$\underline{C}$H$_2$—$\underline{C}$H$_2$—CH$_2$—)$_{sperm}$, 2×N—CH$_2$—$\underline{C}$H$_2$—CH$_2$—N, 2×C(4)H$_2$—C(7)H$_2$, 2×C(12)H$_2$—C(16)H$_2$; 28.7, 28.8 (4×C(CH$_3$)$_3$); 34.0 (2×C(2)H$_2$); 38.5, 44.6, 46.8, 47.6 (2×N—$\underline{C}$H$_2$—CH$_2$—$\underline{C}$H$_2$—N, (CH—CH$_2$—CH$_2$—$\underline{C}$H$_2$—)$_{sperm}$, ($\underline{C}$H(CH$_2$O$_2$C—R)$_2$); 59.5 (CO—$\underline{C}$H); 62.8 (CH($\underline{C}$H$_2$O$_2$C—R)$_2$); 79.5, 80.1, 81.5 (4×CO—O—$\underline{C}$(CH$_3$)$_3$); 130.07, 130.37 (2×$\underline{C}$H=$\underline{C}$H); 156.3 (4×CO—O—C(CH$_3$)$_3$); 173.7 ($\underline{C}$O—NH, 2×CH$_2$—$\underline{C}$OO).

EXAMPLE 12

Synthesis of 2-(6-carboxy-spermyl)-1,3-dioleoyloxy-propylamide 12

85 mg (68 μmol) 11 was dissolved in 1 ml abs. $CH_2Cl_2$ in a round-bottom flask with bubble counter and 400 μl TFA was added. The reaction mixture was stirred for 45 min. at room temperature. Subsequently ca. 20 ml $CH_2Cl_2$ was added, it was washed with saturated NaHCO$_3$ solution and dried over Na$_2$SO$_4$. After removing the solvent 56 mg (97%) of a colourless oil was obtained.

$^1$H-NMR (CDCl$_3$): δ=0.8–0.95 (m; 6 H; 2×CH$_2$—C$\underline{H}_3$); 1.15–1.4 (m; 40 H; 2×CO—(CH$_2$)$_2$—(C$\underline{H}_2$)$_4$, 2×(C$\underline{H}_2$)$_6$—CH$_3$); 1.5–1.9 (m; 12 H; 3×(—CH$_2$—C$\underline{H}_2$—CH$_2$—)$_{sperm}$, 2×CO—CH$_2$—C$\underline{H}_2$—, (—CH—C$\underline{H}_2$—CH$_2$—)$_{sperm}$); 1.9–2.1 (m, 8 H; 2×C$\underline{H}_2$—CH=CH—CH$_2$); 2.2–2.35 (m; 4 H; 2×CO—C$\underline{H}_2$); 2.45–3.3 (m; 10 H; 5×N—C$\underline{H}_2$); 4.0–4.59 (m; 12 H; 2×C$\underline{H}$—N, (CH(C$\underline{H}_2$O$_2$C—R)$_2$, 2×NH$_2$, 2×NH$_{sperm}$); 5.25–5.45 (m; 4 H; 2×C$\underline{H}$=C$\underline{H}$); 7.6–7.9 (s(broad); 1 H; N$\underline{H}$—CO).

$^{13}$C-NMR (CDCl$_3$): δ=14.0 (2×C(18)H$_3$); 22.5 (2×C(17)H$_2$); 24.7 (2×C(3)H$_2$); 27.0, 27.1 (C(8)H$_2$, C(11)H$_2$); 29.0, 29.1, 29.2, 29.4, 29.60, 29.61, 31.8 ((CH—$\underline{C}$H$_2$—$\underline{C}$H$_2$—CH$_2$—)$_{sperm}$, 2×N—CH$_2$—$\underline{C}$H$_2$—CH$_2$—N, 2×C(4)H$_2$—C(7)H$_2$, 2×C(12)H$_2$—C(16)H$_2$); 33.9 (2×C(2)H$_2$); 41.0, 47.3, 48.8 (2×N—$\underline{C}$H$_2$—CH$_2$—$\underline{C}$H$_2$—N, (CH—CH$_2$—CH$_2$—$\underline{C}$H$_2$—)$_{sperm}$, ($\underline{C}$H(CH$_2$O$_2$C—R)$_2$); 62.0, 62.9 (CO—$\underline{C}$H, CH($\underline{C}$H$_2$O$_2$C—R)$_2$); 129.5, 129.9 (2×$\underline{C}$H=$\underline{C}$H); 173.4, 174.2 ($\underline{C}$O—NH, 2×CH$_2$—$\underline{C}$COO).

EXAMPLE 13

Synthesis of 2-dimethylamino-1,3-propanediol 13

456 mg (5 mmol) 2-amino-1,3-propanediol was placed in a round-bottom flask and admixed with 1.13 ml (25 mmol) formic acid (85%, d=1.20) while cooling on ice. Subsequently 895 μl (12 mmol) formaldehyde (37%) was added and the mixture was heated for 10 h to 80° C. in a water bath. After cooling 3 ml 2 N hydrochloric acid was added. The product was isolated by chromatography over 25 g acidic ion exchanger (DOWEX). The crude product obtained in this manner was purified by short-path distillation in an oil pump vacuum. 253 mg (42%) of a colourless oil was obtained.

Boiling point$_{1mbar}$=105° C.

$^1$H-NMR (DMSO-d$_6$): δ=2.25 (s; 6 H; N(C$\underline{H}_3$)$_2$); 2.31–2.45 (m, 1 H; C$\underline{H}$(CH$_2$OH)$_2$); 3.35–3.55 (m, 4 H; CH(C$\underline{H}_2$OH)$_2$); 4.24 (s(broad); 2 H; CH(CH$_2$O$\underline{H}$)$_2$).

$^{13}$C-NMR (DMSO-d$_6$): δ=41.8 (N($\underline{C}$H$_3$)$_2$); 58.7 (CH($\underline{C}$H$_2$OH)$_2$); 66.7 ($\underline{C}$H(CH$_2$OH)$_2$).

EXAMPLE 14

Synthesis of 2-dimethylamino-(1,3-dioleoyloxy)-propane 14

A solution of 183 mg (1.54 mmol) 13, 1.088 g (3.85 mmol) oleic acid, 795 mg (3.85 mmol) DCC and 18 mg (154 μmol) dimethylaminopyridine in 20 ml abs. $CH_2Cl_2$ was stirred overnight at room temperature. Subsequently it was filtered, rewashed with hexane/ether (3:1) and the filtrate was rotary evaporated. After column chromatography on silica gel, ($CH_2Cl_2$/MeOH=30:1) 444 mg (45%) of the product was obtained as a colourless oil.

$^1$H-NMR (CDCl$_3$): δ=0.85–0.95 (m; 6 H; 2×CH$_2$—C$\underline{H}_3$); 1.2–1.4 (m; 40 H; 2×CO—(CH$_2$)$_2$—(C$\underline{H}_2$)$_4$, 2×(CH$_2$)$_6$—C$\underline{H}_3$); 1.55–1.7 (m; 4 H; 2×CO—CH$_2$—C$\underline{H}_2$—); 1.95–2.05 (m; 8 H; 2×C$\underline{H}_2$—CH=CH—C$\underline{H}_2$); 2.3–2.35 (m, 4 H; 2×CO—C$\underline{H}_2$—CH$_2$—); 2.39 (s; 6 H; N(C$\underline{H}_3$)$_2$); 2.9–3.0 (m; 1 H; C$\underline{H}$(CH$_2$O$_2$C—R)$_2$); 4.1–4.3 (m; 4 H; CH(C$\underline{H}_2$O$_2$C—R)$_2$); 5.3–5.4 (m; 4 H; 2×C$\underline{H}$=C$\underline{H}$).

$^{13}$C-NMR (CDCl$_3$): δ=14.4 (2×C(18)H$_3$); 23.0 (2×C(17)H$_2$); 25.3 (2×C(3)H$_2$); 27.55, 27.6 (C(8)H$_2$; C(11)H$_2$); 29.50, 29.53, 29.67, 29.7, 29.8, 29.9, 30.06, 30.14, 32.3 (2×C(4)H$_2$—C(7)H$_2$, 2×C(12)H$_2$—C(16)H$_2$); 34.7 (2×C(2)H$_2$); 42.4 (N($\underline{C}$H$_3$)$_2$); 61.6, 61.9 ($\underline{C}$H($\underline{C}$H$_2$O$_2$C—R)$_2$); 130.09, 130.36 (2×$\underline{C}$H=$\underline{C}$H); 173.9 (CH$_2$—$\underline{C}$OO).

EXAMPLE 15

Synthesis of N-[2-(1,3-dioleoyloxy)propyl]-N,N,N-trimethylammoniummethyl sulfate 15

66 μl (696 μmol) dimethyl sulfate was added at 0° C. to a solution of 200 mg (309 μmol) 14 in 1.55 ml ethyl acetate/hexane (1:1) and the reaction mixture was stirred for 24 h at 4° C. Subsequently the solvent was removed. 213 mg (89%) of a colourless oil was obtained.

$^1$H-NMR (CDCl$_3$): δ=0.75–0.9 (m; 6 H; 2×CH$_2$—C$\underline{H}_3$); 1.05–1.4 (m; 40 H; 2×CO—(CH$_2$)$_2$—(C$\underline{H}_2$)$_4$, 2×(C$\underline{H}_2$)$_6$—CH$_3$); 1.4–1.65 (m; 4 H; 2×CO—CH$_2$—C$\underline{H}_2$—); 1.8–2.1 (m; 8 H; 2×C$\underline{H}_2$—CH=CH—C$\underline{H}_2$); 2.25–2.4 (m, 4 H; 2×CO—C$\underline{H}_2$—CH$_2$—); 3.3–3.45 (s(broad); 9 H; N(C$\underline{H}_3$)$_3$); 3.61 (s; 3 H; C$\underline{H}_3$—O—S); 4.1–4.2 (m; 1 H; C$\underline{H}$(CH$_2$O$_2$C—R)$_2$); 4.4–4.65 (m; 4 H; CH(CH$_2$O$_2$C—R)$_2$); 5.2–5.4 (m; 4 H; 2×C$\underline{H}$=C$\underline{H}$).

$^{13}$C-NMR (CDCl$_3$): δ=13.8 (2×C(18)H$_3$); 22.4 (2×C(17)H$_2$); 24.4 (2×C(3)H$_2$); 26.9, 27.0 (C(8)H$_2$; C(11)H$_2$); 28.8, 28.9, 29.0, 29.05, 29.3, 29.46, 29.5, 31.6 (2×C(4)H$_2$—C(7)H$_2$, 2×C(12)H$_2$—C(16)H$_2$); 33.6 (2×C(2)H$_2$); 53.0, 54.0 (N($\underline{C}$H$_3$)$_3$, $\underline{C}$H$_3$—O—S); 58.7 (CH($\underline{C}$H$_2$O$_2$C—R)$_2$); 69.8 ($\underline{C}$H(CH$_2$O$_2$C—R)$_2$); 129.4, 129.8 (2×$\underline{C}$H=$\underline{C}$H); 172.3 (CH$_2$—$\underline{C}$OO).

EXAMPLE 16

N,N',N'',N'''-tetra-tert.-butyloxycarbonyl-6-carboxyspermyl-2,3-dihydroxy-1-propylamide 16

A solution of 300 mg (0.47 mmol) tetra-Boc-carboxyspermine in 4 ml dichloromethane was successively admixed with 59 mg (0.51 mmol) hydroxysuccinimide dissolved in 2 ml dichloromethane/THF (1:1) and 106 mg (0.51 mmol) dicyclohexyl-carbodiimide dissolved in 2.2 ml dichloromethane and stirred for 4 days at room temperature. After removing the solvent the residue was taken up in ethyl acetate, filtered and the solvent was removed from the clear filtrate. The residue (335 mg (0.45 mmol) tetra-Boc-carboxyspermine-hydroxysuccinimidyl ester) was taken up in 2.18 ml dimethylformamide and admixed with 41 mg (0.45 mmol) (±)-1-amino-2,3-propanediol and 61.5 μl (0.45 mmol) triethylamine. After stirring for 3 days the solvent was removed and the residue was partitioned between ether and water. The organic phase is dried. After removing the solvent an oily product was obtained which can be processed directly.

EXAMPLE 17

Synthesis of N,N',N'',N'''-tetra-tert.-butyloxycarbonyl-6-carboxy-spermyl-2,3-dioleoyloxy-1-propylamide 17

218 mg (0.77 mmol) oleic acid, 180 mg (0.87 mmol) dicyclohexylcarbodiimide and a catalytic amount of dimethylaminopyridine was added to a solution of 252 mg (0.35 mmol) 16 in 1.4 ml carbon tetrachloride. It was stirred overnight. After removing the solvent the residue was chromatographed (silica gel, dichloromethane with an increasing content of methanol up to 10%). 392 mg (90% of theory) of an oil was obtained.

$^{13}$C-NMR: δ=173.8, 173.3 (oleic acid-C=O), 156 (C(=O)—N, 130.0,129.7 (oleic acid C=C), 80.97, 79.67, 79.84 (quart.-BOC), 70.3 (Glyc. sn2), 62.6 (Glyc. sn1), 59.1 (sperm.-), 46.5, 44.3, 43.7, 43.1 (sperm. N—CH$_2$), 39.5 (Glyc. sn3), 38.2 (sperm. N—CH$_2$), 34.9 (oleic acid C-2), 31.9 (oleic acid C-16), 29.8–29.1 (oleic acid-CH$_2$), 28.4 (BOC-CH$_3$), 27.2 (oleic acid C-8,11), 25.0 (oleic acid C-3), 22.7 (oleic acid C-17), 14.1 (oleic acid C-18).

EXAMPLE 18

(6-Carboxy-spermyl)-2,3-dioleoyloxy-1-propylamide 18

A solution of 195 mg (0.16 mmol) 17 in 5 ml dichloromethane was admixed at room temperature with 5 ml TFA. After 20 min stirring it was diluted with 100 ml dichloromethane and washed with saturated sodium hydrogen carbonate solution. The combined organic phases were dried and the solvent was evaporated. 134 mg (99%) of a viscous oil was obtained.

$^1$H-NNR (500 MHz, CDCl$_3$/CD$_3$COOD 5:1) δ=5.33 (oleic acid 9, 10-H), 5.16 (glycerol 2-H), 4.25 and 4.06 (glycerol 1-H), 4.15 (spermine-H), 3.55 and 3.33 (glycerol 3-H), 3.18 and 3.05 (spermine N—CH$_2$), 2.31 (oleic acid 2-H), 2.21 (spermine —CH$_2$), 2.01 (oleic acid 8, 11-H), 1.98 (spermine-), 1.83 (spermine CH$_2$), 1.57 (oleic acid 3-H), 1.30 (oleic acid 4–7, 12–17-H), 0.87 ppm (oleic acid 18-H).

$^{13}$C-NMR: δ=173.82 and 173.53 (oleic acid C-1), 154.06 (C(=O)—N), 130.17 and 129.81 (oleic acid C-9 and C-10), 70 (glycerol C-2), 63.2 (glycerol C-1), 39.8 (glycerol C-3), 34.25, 34.05, 33.97 (oleic acid C-2), 32.70, 31.93 (oleic acid C-16), 30.82, 29.79, 29.57 and 29.35 (oleic acid CH$_2$), 27.25 (oleic acid C-8, 11), 25.64, 25.53, 25.32, 24.97 (oleic acid C-3), 24.71, 22.70 (oleic acid C-17), 14.13 ppm (oleic acid C-18). MS (FAB): MH$^+$: 848.6 (calc. 848.8).

EXAMPLE 19

Synthesis of N-((N-Boc)-glycyl)-aminopropane-2,3-diol 19

10.00 g (36.73 mmol) Boc-Gly-Osu (Bachem) was dissolved together with 3.35 g (36.77 mmol) 1-amino-2,3-propanediol in 50 ml DMF and stirred for 18 h. The product was purified by flash chromatography (CH$_2$Cl$_2$/MeOH; 95:5 v/v). 8.94 g (98%) 19 was obtained as a colourless oil.

$^1$H-NMR (CDCl$_3$): δ=1.45 (s; 9 H; CH$_3$); 3.28 (m; 1 H; CH$_2$—OH;); 3.39 (m; 1 H; CH$_2$—OH;); 3.35 (m; 1 H; CH$_2$—N$_{aminoprop.}$); 3.38 (m; 1 H; CH$_2$—N$_{aminoprop.}$); 3.78 (s; 3 H; CH—OH; CH$_2$—NH$_{gly}$); 4.41 (br s; 1 H; OH); 4.67 (br s; 1 H; OH); 6.04 (tr; 1 H; NH); 7.45 (tr; 1 H; NH).

$^{13}$C-NMR (CDCl$_3$): δ=28.4 (CH$_3$); 42.2 (CH$_2$—N$_{gly}$); 44.0 (CH$_2$—N$_{aminoprop.}$); 64.0 (CH$_2$—OH); 70.8 (CH—OH); 80.3 (quart. C$_{Boc}$); 156.6 (NCO$_2$); 174.5 (NCO).

EXAMPLE 20

Synthesis of 2,3-dioleoyloxy-N-((N-Boc)-glycyl)-aminopropane 20

8.90 g (35.85 mmol) 19 was dissolved together with 22.70 g (110.02 mmol) DCC and 26.60 g (94.17 mmol) oleic acid in 50 ml DMF. 0.42 g (3.44 mmol) DMAP was added and stirred for 2 d. Afterwards it was filtered, rotary evaporated and the product was purified by chromatography (CH$_2$Cl$_2$/MeOH; 99:1 v/v). Yield 19.25 g 20 as a colourless oil (69%).

$^1$H-NMR (CDCl$_3$): δ=0.89 (tr; 6 H; CH$_{3, \; oleic \; acid}$); 1.30 (br s; 40 H; C—CH$_2$—C); 1.45 (br s; 9 H; CH$_{3, \; Boc}$); 1.62 (m; 4 H; CH$_2$—CH$_2$C=O); 2.03 (m; 8 H; CH$_2$—CH=CH); 2.32 (tr; 4 H; CH$_2$C=O); 3.42–3.57 (m; 2 H; CH$_2$—N$_{aminoprop.}$); 3.75 (d; 2 H; CH$_2$—N$_{gly}$); 4.12 (dd; 1 H; CH$_2$—O$_{aminoprop.}$); 4.27 (dd; 1 H; CH$_2$—O$_{aminoprop.}$); 5.08 (m; 1 H; CH—O); 5.20 (s, 1 H; NH); 5.34 (m; 4 H; CH=CH); 6.58 (tr; 1 H; NH).

$^{13}$C-NMR (CDCl$_3$): δ=14.0 (CH$_{3, \; oleic \; acid}$); 22.7 (CH$_{2, \; oleic \; acid}$); 24–9 (CH$_{2, \; oleic \; acid}$); 27.2 (CH$_{2, \; oleic \; acid}$); 27.2 (CH$_{2, \; oleic \; acid}$); 28.3 (CH$_{2, \; oleic \; acid}$); 29.2 (CH$_{2, \; oleic \; acid}$); 29.3 (CH$_{3, \; Boc}$); 29.5 (CH$_{2, \; oleic \; acid}$); 29.8 (CH$_{2, \; oleic \; acid}$); 31.9 (CH$_{2, \; oleic \; acid}$); 34.0 (CH$_{2, \; oleic \; acid}$); 34.2 (CH$_{2, \; oleic \; acid}$); 39.7 (CH$_2$—N$_{gly}$); 44.5 (CH$_2$—N$_{aminoprop.}$); 62.7 (CH$_2$—O$_{aminoprop.}$); 70.2 (CH—O$_{aminoprop.}$); 80.3 (quart. C$_{Boc}$); 129.7 (CH=CH); 129.7 (CH=CH); 130.0 (CH=CH); 130.0 (CH=CH); 156.1 (NCO$_2$); 169.8 (NCO); 173.2 (CO$_{oleic \; acid}$); 173.4 (CO$_{oleic \; acid}$).

EXAMPLE 21

Synthesis of 2,3-dioleoyloxy-N-(glycyl)-aminopropane 21

15.20 g (19.56 mmol) 20 was taken up in 200 ml CH$_2$Cl$_2$/TFA (3:1 v/v) and stirred for 30 min. Afterwards the solution was diluted with 200 ml CH$_2$Cl$_2$ and shaken out with 200 ml sat. NaHCO$_3$ solution. The organic phase was dried over MgSO$_4$ and rotary evaporated. Yield: 11.64 g (88%) 21 as an oil.

$^1$H-NMR (CDCl$_3$): δ=0.88 (tr; 6 H; CH$_3$); 1.29 (br s; 40 H; C—CH$_2$—C); 1.62 (m; 4 H; CH$_2$—CH$_2$C=O); 1.82 (s; 2 H CH$_2$—N$_{gly}$); 2.01 (m; 8 H; CH$_2$—CH=CH); 2.32 (tr; tr; 4 H; CH$_2$C=O); 3.36 (s; 2 H; NH$_2$); 3.43–3.62 (m; 2 H; CH$_2$—N$_{aminoprop.}$); 4.12 (dd; 1 H; CH$_2$—O$_{aminoprop.}$); 4.28 (dd; 1 H; CH$_2$—O$_{aminoprop.}$); 5.14 (m; 1 H; CH—O$_{aminoprop.}$); 5.34 (m; 4 H; CH=CH); 7.60 (tr; 1 H; NH).

$^{13}$C-NMR (CDCl$_3$): δ=14.0 (CH$_3$); 22.6 (CH$_{2, \; oleic \; acid}$); 24.8 (CH$_{2, \; oleic \; acid}$); 24.8 (CH$_{2, \; oleic \; acid}$); 27.1 (CH$_{2, \; oleic \; acid}$); 29.0 (CH$_{2, \; oleic \; acid}$); 29.1 (CH$_{2, \; oleic \; acid}$); 29.2 (CH$_{2, \; oleic \; acid}$); 29.4 (CH$_{2, \; oleic \; acid}$); 29.6 (CH$_{2, \; oleic \; acid}$); 31.8 (CH$_{2, \; oleic \; acid}$); 34.0 (CH$_{2, \; oleic \; acid}$); 34.2 (CH$_{2, \; oleic \; acid}$); 39.1 (CH$_2$—N$_{gly}$); 44.5 (CH$_2$—N$_{aminoprop.}$);

62.7 ($CH_2-N_{aminoprop.}$); 129.6 ($CH_{oleic\ acid}$); 129.9 ($CH_{oleic\ acid}$); 173.1 (NCO); 173.1 ($CO_{oleic\ acid}$); 173.3 ($CO_{oleic\ acid}$).

EXAMPLE 22

Synthesis of 2,3-dioleoyloxy-N-(N-(N,N',N'',N'''-tetra-tert.-butyloxycarbonyl-6-carboxy-spermyl)-glycyl)-aminopropane 22

100 mg (0.15 mmol) 21 was dissolved together with 102 mg (0.16 mmol) (Boc)$_4$-spermyl-COOH and 39 mg (0.19 mmol) DCC in 1 ml $CH_2Cl_2$ and stirred for 18 h. Afterwards precipitated DCH was removed by filtration. Concentration by evaporation and chromatographic purification ($CH_2Cl_2$/MeOH, 97:3) yielded 123.1 mg (63%) 22 as a colourless oil.

$^1$H-NNR ($CDCl_3$+0.1 ml $CD_3COOD$): δ=0.88 (tr; 6 H; $CH_{3,\ oleic\ acid}$); 1.28 (br s; 40 H; C—$CH_2$—$C_{oleic\ acid}$); 1.46 (br s; $CH_{3,Boc}$; $CH_{2,spermyl}$); 1.62 (m; 4 H; $C\underline{H}_2CH_2C=O$); 2.03 (m; 8 H; $C\underline{H}_2$—CH=CH); 2.32 (m; 4 H; $C\underline{H}_2C=O$); 3.00–3.33 (m; 10 H; $CH_{2,\ spermyl}$); 3.33–3.62 (m; 2 H; $CH_2-N_{aminoprop.}$); 3.95 (m; 2 H; $CH_2-N_{gly}$); 4.10 (m; 1 H; $CH_2-O$); 4.28 (m; 1 H; $CH_2-O$); 4.30 (br s; 1 H; $CH_{spermyl}$); 5.12 (m; 1 H; $CH_{aminoprop.}$); 5.35 (m; 4 H; CH=CH).

$^{13}$C-NMR ($CDCl_3$+0.1 ml $CD_3COOD$): δ=14.1 ($CH_{3,\ oleic\ acid}$); 22.8 ($CH_{2,\ oleic\ acid}$); 25–0 ($CH_{2,\ oleic\ acid}$); 27.3 ($CH_{2,\ oleic\ acid}$); 27–3 ($CH_{2,\ oleic\ acid}$); 28.4 ($CH_{3,\ Boc}$); 28.5 ($CH_{3,\ Boc}$); 29.3 ($CH_{2,\ oleic\ acid}$); 29.3 ($CH_{2,\ oleic\ acid}$); 29.4 ($CH_{2,\ oleic\ acid}$); 29.7 ($CH_{2,\ oleic\ acid}$); 29.9 ($CH_{2,\ oleic\ acid}$); 32.0 ($CH_{2,\ oleic\ acid}$); 34.2 ($CH_{2,\ oleic\ acid}$); 39.7 ($CH_2-N_{gly}$); 43.1 ($CH_2-N_{aminoprop.}$); 63.0 ($CH_2-O$); 70.2 (CH—O); 79.6 (quart. $C_{Boc}$); 80.2 (quart. $C_{Boc}$); 80.9 (quart. $C_{Boc}$); 81.5 (quart. $C_{Boc}$); 129.8 (CH=CH); 130.1 (CH=CH); 155–158 ($NCO_2$); 173.6 (COO); 173.8 (COO).

EXAMPLE 23

Synthesis of 2,3-dioleoyloxy-N-(N-(6-carboxy-spermyl)-glycyl)-aminopropane 23

1.00 g (0.77 mmol) 22 was dissolved in 100 ml $CH_2Cl_2$/TFA (3:1) and stirred for 30 min. Subsequently the solvent was removed. 1.03 g (98.80%) 23 was obtained as a wax-like product.

$^1$H-NMR (d$_6$-DXSO): δ=0.85 (tr; 6 H; $CH_{3,oleic\ acid}$); 1.23 (br s; 44 H; C—$CH_2$—$C_{oleic\ acid/spermyl}$); 1.50 (m; 4 H; C$\underline{H}_2$—$CH_2C=O$); 1.67 (m; 2 H; C—$CH_2$—$C_{spermyl}$); 1.83 (m; 2 H; C—$CH_2$—$C_{spermyl}$); 1.95 (m; 8 H; C$\underline{H}_2$—CH=CH); 2.23 (m; 4 H; $C\underline{H}_2C=O$); 2.82–3.30 (m; 10 H; $CH_{2,\ spermyl}$); 3.26 (m; 1 H; $CH_2-N_{aminoprop.}$); 3.36 (m; 1 H; $CH_2-N_{aminoprop.}$); 3.74–3.88 (m; 2 H; $CH_2-N_{gly}$); 3.93 (br s; 1 H; $CH_{spermyl}$); 4.01 (m; 1 H; $CH_2-O$); 4.24 (m; 1 H; $CH_2-O$); 5.02 (m; 1 H; $CH_{aminoprop.}$); 5.31 (m; 4 H; CH=CH); 8.10 (br s; 6 H; NH); 8.33 (tr; 1 H; NHC=O); 8.98 (br s; 2 H; NH); 9.04 (tr; 1 H; NHC=O); 9.15 (br s; 1 H; NH); 9.50 (br s; 1 H; NH).

$^{13}$C-NMR (d$_6$-DMSO): δ=13.8 ($CH_{3,oleic\ acid}$); 20.9 ($CH_{2,\ sper}$); 22.1 ($CH_{2,\ oleic\ acid}$); 23.8; 23.9 ($CH_{2,\ sper}$); 24.4; 26.6 ($CH_{2,\ oleic\ acid}$); 26.9 ($CH_{2,\ sper}$); 28.5–29.1 ($CH_{2,\ oleic\ acid}$); 31.3 ($CH_{2,\ oleic\ acid}$); 33.4, 33.6 ($CH_{2,oleic\ acid}$); 36.2 ($CH_{2,\ sper}$); 38.7 ($CH_{2,\ sper}$); 41.8 ($CH_2-N_{gly}$); 43.0 ($CH_2-N_{aminoprop.}$); 43.9, 46.2 ($CH_{2,\ sper}$); 58.8 ($CH_{sper}$); 62.8 ($CH_2-O$); 129.5 (CH=CH); 129.6 (CH=CH); 167.4, 168.5 ($NCO_{sper/gly}$); 172.2 (COO); 172.4 (COO).

EXAMPLE 24

Transfection of Adherent HELA Cells with CAT Plasmid

1. Starting Material
   1. Medium for the HELA stock culture (ATTC No. CCL 2): MEM (with EARL's salts), 10% FCS, 2 mM pyruvate, 2 mM glutamine, 1×n.e. amino acids.

For the transfection prepare the same medium containing 5% FCS and the same medium without FCS.

2. pSV2-CAT plasmid in TE buffer, concentration: 1 mg/ml, 5 kb. (Gorman C. M. et al., Mol. Cell. Biol. 2, 1044–1051(1982)).

3. New transfection reagents:
   in MES (20 mM MES, 150 mM NaCl, pH 6.2) concentration 1.0 mg/ml, sonicated (Branson sonifier) and sterilized by filtration or
   in 99.8% EtOH, concentration 2.5 mg/ml (not sonicated and not sterilized by filtration)

4. HEPES: 20 mM Hepes, 150 mM NaCl, pH 7.4, sterile
   5. PBS, BM order No. 210 331 (10 mM buffer, 150 mM salt), sterile and unsterile
   6. 150 mM NaCl,
   7. lysis buffer: 10 mM MOPS, NaCl 10 mM, 1 mM EGTA, 1% mM Triton X-100, pH 6.5.

2. Transfection Mixture

One day before transfection the cells were transferred to 6 cm petri dishes: for this the cells were trypsinized and diluted to 2×10$^5$ cells/ml (cell count determined with a Neubauer counting chamber) in medium containing 5% FCS. 5 ml per dish. Incubation in an incubator (at 37° C., 5% $CO_2$).

Mixture Per Dish for Aqueous Solutions of the Transfection Reagent (TR):

1. Add HEPES to 5 μg plasmid (=5 μl) to a final volume of 100 μl and vortex.
2. Add HEPES to 10–40 μg TR (=10–40 μl) to a final volume of 100 μl and vortex.
3. Combine the solutions from 1. and 2., shake carefully. Allow to stand for 10 to 15 min at RT.
4. During the incubation period change the medium in the test dishes: aspirate the old medium and replace with 3 ml medium (containing 5% FCS or, if without FCS, wash cells twice with PBS).
5. Add plasmid-TR mixture from 3 (200 μl) directly to the fresh medium (with or without FCS) and disperse evenly by carefully swirling the dish.
6. Incubate for 6 h in an incubator (at 37° C., 5% $CO_2$).
7. Then supplement the medium to a final concentration of FCS of 5–10%. Final medium volume 6 ml.
8. Incubate for 19 h in an incubator.
9. Then completely aspirate the mixture and replace with 5 ml medium containing 5–10% FCS.

Mixture Per Dish for Ethanolic Solutions of the TR:

A Without FCS in the Medium:

1. 5 μg plasmid (=5 μl)+500 μl medium without FCS, and vortex.
2. 10–40 μg TR (=4–16 μl)+500 μl medium without FCS, and vortex.
3. Wash cells free of FCS: aspirate 5 ml medium and wash twice with PBS; aspirate.
4. Combine solutions from 1. and 2., shake carefully.
5. Place plasmid-TR mixture from 4. (ca. 1020 μl) onto the washed cells and distribute equally by carefully swirling the dish.

6. Incubate for 6 h in an incubator (at 37%, 5% $CO_2$).
7. Then supplement the medium to a final concentration of FCS of 5–10%. Final medium volume 6 ml.
8. Incubate for 18 h in an incubator.
9. Then completely aspirate the mixture and replace by 5 ml medium containing 5–10% FCS.

B With FCS in the Medium
1. 5 μg plasmid (=5 μl)+150 μl NaCl and vortex.
2. 10–40 μg TR (=4–16 μl)+150 μl NaCl and vortex.
3. Combine solutions from 1 and 2, briefly shake carefully. Allow to stand for 15 min at RT.
4. During the incubation period change the medium in the test dishes: aspirate the old medium and replace with 1.5 ml medium (containing 10% FCS).
5. Place plasmid-TR mixture from 3 (ca. 320 μl) onto the fresh medium and distribute equally by carefully swirling the dish.
6. Incubate for 6 h in an incubator (at 37%, 5% $CO_2$).
7. Then supplement the medium to a final concentration of FCS of 5–10%. Final medium volume 6 ml.
8. Incubate for 18 h in an incubator.
9. Then completely aspirate the mixture and replace by 5 ml medium containing 5–10% FCS.

3. Cell Lysis
1. Aspirate the medium and wash the cells three times with ice-cold PBS.
2. Carefully aspirate residual liquid and add 1 ml lysis buffer per dish. Incubate for 30 min at RT, allow the dishes to stand without shaking.
3. Remove the cell lysate by pipette and transfer to 1.5 ml Eppendorf tubes.
4. Centrifuge the lysates in a bench centrifuge, 3 min.
5. Remove the supernatant and transfer into a fresh vessel. Discard the pellet.

4. Protein Determination of the Lysates

The protein determination is carried out after the lysis.

The protein determination is analysed according to Bradford (M. Bradford, Anal. Biochem. 72, 248 (1976)).

For the further examination the lysates from an experiment are adjusted with sample buffer (from the CAT-ELISA-kit, Boehringer Mannheim, order No. 1363727) to the same protein concentration (ca. 250 μg/ml).

5. Determination of the Transfection Efficiency

The lysates are examined in a CAT-ELISA (Boehringer Mannheim, order No. 1363727). 200 μl of each of the lysates adjusted to the same protein concentration is used in the ELISA.

Comparison of the absorbances yields information about the transfection efficiency.

Reconstitution of the Kit Components and Dilution to Working Concentration:

1. CAT Standard, Bottle 1

Add 0.5 ml redistilled water to a bottle of lyophilisate and dissolve by shaking. The concentration (ng/ml) is printed on the label.

Working Dilution:

Dilute the dissolved lyophilisate (cf. bottle label for the concentration) with sample diluent buffer (bottle 7) to 1.0, 0.5, 0.25, 0.125, 0.0625, 0.0312, 0 ng/ml.

2. PAB<CAT> Dig, Bottle Z

Add 0.5 ml redistilled water to a bottle of lyophilisate and dissolve by shaking (concentration=0.2 mg/ml).

Working Dilution:

Dilute the dissolved lyophilisate (0.2 mg/ml) with sample diluent buffer (bottle 7) to 2 μg/ml.

3. PAB<Dig> POD, Bottle 3

Add 0.5 ml redistilled water to a bottle of lyophilisate and dissolve by shaking (concentration=20 U/ml).

Working Dilution:

Dilute the dissolved lyophilisate (20 U/ml) with sample diluent buffer (bottle 7) to 150 mU/ml.

4. Washing Buffer, Bottle 6

Ready-to-use washing buffer is prepared by mixing 1 part 10× washing buffer (bottle 6) with 9 parts redistilled water. 1× washing buffer is required for all washing steps.

5. Sample Diluent Buffer, Bottle 7

Bring bottle no. 7 to RT in a water bath. Ready to use.

6. POD Substrate, Bottle 4

ABTS 1-component substrate (bottle No. 4), ready to use, temperature kept constant at RT.

Procedure

The following table refers to the buffers and working dilutions mentioned above. The MTP modules are tapped out on multiple cellulose paper layers after each washing step.

For the 37° C. incubation steps an MTP cover foil is stuck onto the plate.

| | Working step | Volume | Time | Temp. | shaking |
|---|---|---|---|---|---|
| 1. | remove MTP module strip | | | | – |
| 2. | CAT enzyme standard, working dilutions or cell lysates | 200 μl/well | 60 min | 37° C. | – |
| 3. | discard, wash 3 times with washing buffer, tap out | 300 μl/well | | 18–25° C. | – |
| 4. | PAB<CAT>DIG working dilution | 200 μl/well | 60 min | 37° C. | – |
| 5. | discard, wash 3 times with washing buffer, tap out | 300 μl/well | | 18–25° C. | – |
| 6. | PAB<DIG>POD working solution | 200 μl/well | 60 min | 37° C. | – |
| 7. | discard, wash 3 times with washing buffer, tap out | 300 μl/well | | 18–25° C. | – |
| 8. | substrate solution | 200 μl/well | 10 min | 18–25° C. | + |
| 9. | measure at 405 nm after ca. 10 min substrate incubation | | | | |

The results are shown in FIGS. 1 and 2.

We claim:

1. A compound of the formula (I)

(I)

in which

R$_1$ is a saturated or unsaturated C(O)—C$_{1-23}$ or saturated or unsaturated C$_{1-24}$ chain, A is selected from A$_1$ and A$_2$ A$_1$ is an O—R$_2$ group in which R$_2$ has the meaning stated for R$_1$ and can be the same as or different from R$_1$, A$_2$ is an NR$_3$X or an N$^+$R$_3$R$_4$R$_5$Y$^-$ residue in which R$_3$, R$_4$ are independently selected from the group consisting of hydrogen, an alkyl group with 1 to 4 C atoms, a (CH$_2$)$_n$—OH and a (CH$_2$)$_n$—NH$_2$ group where n=2–6, provided that R$_3$ and R$_4$ are not both hydrogen, R$_5$ which can be the same or different from R$_3$ and R$_4$, is hydrogen, an alkyl group with 1 to 4 C atoms, a (CH$_2$)$_n$—OH, a (CH$_2$)$_n$-halogenide or a ((CH$_2$)$_m$NH)$_o$—(CH)$_2$)$_n$ group in which m is an integer from 2 to 6 and is equal to or different from n and o wherein n is a number from 2 to 6 and o is an integer from 0 to 4, X has the meaning for R$_5$ or has the following meaning: an amidically bound amino acid, an amidically bound peptide or polypeptide, a C(O)—CHR$_6$N(R$_7$)$_2$, a C(O)—CHR$_6$N$^+$(R$_7$)$_3$, a C(O)—CHR$_6$N$^+$(R$_7$)$_2$R$_8$ or a C(O)—CHR$_6$NR$_7$R$_8$ group, provided that if R$_3$ X is an amidically bound amino acid, an amino acid derivative, a peptide or polypeptide, wherein, R$_6$ is a (CH$_2$)$_m$—NR$_7$R$_8$, a (CH$_2$)$_m$—N$^+$(R$_7$)$_3$R$_8$ or a (CH$_2$)$_m$—N$^+$(R$_7$)$_2$R$_8$ residue and m is a number from 1 to 5, R$_7$ is hydrogen or an alkyl group with 1 or 4 C atoms, R$_8$ is a (CH$_2$)$_n$—N(R$_7$)$_2$ or (CH$_2$)$_n$—N$^+$(R$_7$)$_3$ group in which n is a number from 2 to 4 and R$_7$ can have the meaning stated above and Y is a pharmaceutically acceptable anion, B is selected from B$_1$ and B$_2$, B$_1$ is an NH[C(O)—(CH$_2$)$_p$—NH]$_q$—Z residue in which p is a number from 1 to 6 and q is a number from 0 to 2,

Z is an amidically bound amino acid, an amidically bound peptide or polypeptide, a C(O)—CHR$_6$N(R$_7$)$_2$, a C(O)—CHR$_6$N$^+$(R$_7$)$_3$, a C(O)—CHR$_6$N$^+$(R$_7$)$_2$R$_8$ or a C(O)—CHR$_6$NR$_7$R$_8$ group wherein R$_6$ to R$_8$ and m have the aforementioned meanings and B$_2$ has the meaning stated for A$_1$ and when A is A$_1$, B is B$_1$ and when A is A$_2$, B is B$_2$.

2. A compound as claimed in claim 1, wherein the residue R$_1$ represents a saturated or unsaturated C$_{10-20}$ or C(O)$_{10-20}$ group.

3. A compound as claimed in claim 1, wherein A$_2$ denotes NR$_3$X in which R$_3$ is hydrogen and X is an amidically bound amino acid, an amino acid derivative, a peptide or polypeptide.

4. A compound of the general formula (I)

(I)

in which

R$_1$ represents a saturated or unsaturated C(O)—C$_{1-23}$ or saturated or unsaturated C$_{1-24}$ chain, A$_1$ represents an O—R$_2$ group in which R$_2$ has the meaning stated for R$_1$ and can be the same as or different to R$_1$ A$_2$ represents an NR$_3$X or an N$^+$R$_3$R$_4$R$_5$Y$^-$ residue in which R$_3$, R$_4$ which can be the same as or different to one another represent hydrogen, an alkyl group with 1 to 4 C atoms, a (CH$_2$)$_n$—OH or a (CH$_2$)$_n$—NH$_2$ group where n=2–6, R$_5$ which can be the same as or different to R$_3$ or R$_4$, denotes hydrogen, an alkyl group with 1 to 4 C atoms, a (CH$_2$)$_n$—OH, a (CH$_2$)$_n$-halogenide, or a ((CH$_2$)$_m$NH)$_o$—(CH$_2$)$_n$—NH$_2$ group in which m is an integer from 2 to 6 and can be equal or different to n or o wherein n can be a number from 2 to 6 and o an integer from 0 to 4, X can, in addition to the meaning for R$_5$, have the following meaning: an amidically bound amino acid, an amidically bound peptide or polypeptide, a C(O)—CHR$_6$N(R$_7$)$_2$, a C(O)—CHR$_6$N$^+$(R$_7$)$_3$, a C(O)—CHR$_6$N$^+$(R$_7$)$_2$R$_8$ or a C(O)—CHR$_6$NR$_7$R$_8$ group in which R$_6$ can be a (CH$_2$)$_m$—NR$_7$R$_8$, a (CH$_2$)$_m$—N$^+$(R$_7$)$_3$ or a (CH$_2$)$_m$—N$^+$(R$_7$)$_2$R$_8$ residue and m can be a number from 1 to 5, R$_7$ represents hydrogen or an alkyl group with 1 to 4 C atoms, R$_8$ represents a (CH$_2$)$_n$—N(R$_7$)$_2$ or (CH$_2$)$_n$—N$^+$(R$_7$)$_3$ group in which n is a number of 2 to 4 and R$_7$ can have the meaning stated above and Y is a pharmaceutically acceptable anion,

B$_1$ represents a NH[C(O)—(CH$_2$)$_p$—NH]$_q$—Z residue in which p is a number from 1 to 5 and q is 0 or 1 and Z represents a C(O)—CHR$_6$N(R7)$_2$, a C(O)—CHR$_6$N$^+$(R7)$_3$, a C(O)—CHR$_6$N$^+$(R7)$_2$R$_8$ group and R$_6$ to R$_8$ and m have the aforementioned meanings B$_2$ can have the meaning stated for A$_1$ and the meaning for A$_1$ is only valid with B$_1$ and that of A$_2$ is only valid with B$_2$.

5. A compound as claimed in claim 1, wherein Y denotes a halogenide, monomethyl sulfate, acetate, trifluoroacetate or phosphate.

6. A compound as claimed in claim 1, wherein said compound is selected from the group consisting of 2-(6-carboxyspermyl)-1,3-dioleoyloxy-propylamide, 1-(6-carboxyspermyl)-2,3-dioleoyloxy-propylamide, 2,3-dioleoyloxy-N-(N-(6-carboxyspermyl)-glycyl)-aminopropane, 2-(6-carboxyspermyl)-1,3-dimyristoyloxy-propylamide, 2-(1,1,1,5,5,10,10,14,14,14-deca-methyl-6-carboxyspermyl)-1,3-dioleoyloxy-propylamide 2-(N,N,N, N',N',N'-hexamethylornithyl)-1,3-dioleoyloxy-propylamide and 2-(N,N,N,N',N',N'-hexamethyllysyl)-1,3-dioleoyloxy-propylamide.

7. A reagent comprising of at least one compound of the general formula (I), and contains a water-miscible solvent and formula (I) is defined as follows:

(I)

in which
$R_1$ represents a saturated or unsaturated $C(O)$—$C_{1-23}$ or saturated or unsaturated $C_{1-24}$ chain, $A_1$ represents an O—$R_2$ group in which $R_2$ has the meaning stated for $R_1$ and can be the same as or different to $R_1$ $A_2$ represents an $NR_3X$ or an $N^+R_3R_4R_5Y^-$ residue in which $R_3$, $R_4$ which can be the same as or different to one another represent hydrogen an alkyl group with 1 to 4 C atoms, a $(CH_2)_n$—OH or a $(CH_2)_n$—$NH_2$ group where n=2–6, $R_5$ which can be the same as or different to $R_3$ or $R_4$, denotes hydrogen, an alkyl group with 1 to 4 C atoms, a $(CH_2)_n$—OH, a $(CH_2)_n$-halogenide or a $((CH_2)_mNH)_o$—$(CH_2)_n$—$NH_2$ group in which m is an integer from 2 to 6 and can be equal or different to n or o wherein n can be a number from 2 to 6 and o an integer from 0 to 4, X can, in addition to the meaning for $R_5$, have the following meaning: an amidically bound amino acid, an amidically bound peptide or polypeptide, a $C(O)$—$CHR_6N(R_7)_2$, a $C(O)$—$CHR_6N^+(R_7)_3$, a $C(O)$—$CHR_6N^+(R_7)_2R_8$ or a $C(O)$—$CHR_6NR_7R_8$ group wherein $R_6$ can be a $(CH_2)_m$—$NR_7R_8$, a $(CH_2)_m$—$N^+(R_7)_3$ or a $(CH_2)_m$—$N^+(R_7)_2R_8$ residue and m can be a number from 1 to 5, $R_7$ represents hydrogen or an alkyl group with 1 to 4 C atoms, $R_8$ represents a $(CH_2)_n$—$N(R_7)_2$ or $(CH_2)_n$—$N^+(R_7)_3$ group in which n is a number from 2 to 4 and $R_7$ can have the meaning stated above and Y is a pharmaceutically acceptable anion, $B_1$ represents an $NH[C(O)$—$(CH_2)_p$—$NH]_q$—Z residue in which p is a number from 1 to 6 and q is a number from 0 to 2, Z represents an amidically bound amino acid, an amidically bound peptide or polypeptide, a $C(O)$—$CHR_6N(R_7)_2$, a $C(O)$—$CHR_6N^+(R_7)_3$, a $C(O)$—$CHR_6N^+(R_7)_2R_8$ or a $C(O)$—$CHR_6NR_7R_8$ group and $R_6$ to $R_8$ and m have the aforementioned meanings and $B_2$ can have the meaning stated for $A_1$ and the meaning for $A_1$ is only valid with $B_1$ and that of $A_2$ is only valid with $B_2$.

8. A reagent as claimed in claim 7, further comprising at least one lipidic compound in at least one water-miscible solvent.

9. A reagent as claimed in claim 7, wherein the water-miscible solvent is a lower alcohol.

10. A reagent comprising at least one compound as claimed in claim 1 in the form of liposomes or other aggregates.

11. A method for the delivery of molecules into cells, comprising contacting a reagent of claim 7 with an anionic biomolecule and subsequently with cells for transfection.

12. A method as claimed in claim 11, wherein the molecules comprise at least one of DNA and RNA.

13. A method as claimed in claim 11, wherein the anionic biomolecule is DNA or a corresponding fragment.

14. A method as claimed in claim 11, wherein said at least one compound in said reagent is selected from the group consisting of 2-(6-carboxyspermyl)-1,3-dioleoyloxy-propylamide, 1-(6-carboxyspermyl)-2,3-dioleoyloxy-propylamide, 2,3-dioleoyloxy-N-(N-(6-carboxyspermyl)-glycyl)-aminopropane, 2-(6-carboxyspermyl)-1,3-dimyristoyloxy-propylamide, 2-(1,1,1,5,5,10,10,14,14,14-deca-methyl-6-carboxyspermyl)-1,3-dioleoyloxy-propylamide 2-(N,N,N,N',N',N'-hexamethylornithyl)-1,3-dioleoyloxy-propylamide and 2-(N,N,N,N',N',N'-hexamethyllysyl)-1,3-dioleoyloxy-propylamide.

15. A reagent as recited in claim 10, further comprising at least one other lipidic compound.

16. A method as recited in claim 14, wherein said reagent further comprises at least one other lipidic compound.

* * * * *